United States Patent
Pu et al.

(10) Patent No.: US 11,981,920 B2
(45) Date of Patent: May 14, 2024

(54) MODIFIED CELL WITH ENHANCED MIGRATION CAPABILITY

(71) Applicant: Innovative Cellular Therapeutics Co., Ltd., Shanghai (CN)

(72) Inventors: Chengfei Pu, Shanghai (CN); Zhiyuan Cao, Shanghai (CN); Lei Xiao, Shanghai (CN); He Sun, Shanghai (CN)

(73) Assignee: Innovative Cellular Therapeutics Holdings, Ltd., George Town (KY)

( * ) Notice: Subject to any disclaimer, the term of this patent is extended or adjusted under 35 U.S.C. 154(b) by 912 days.

(21) Appl. No.: 16/701,917

(22) Filed: Dec. 3, 2019

(65) Prior Publication Data

US 2020/0172865 A1 Jun. 4, 2020

Related U.S. Application Data

(60) Provisional application No. 62/775,168, filed on Dec. 4, 2018.

(51) Int. Cl.
| | |
|---|---|
| *C12N 5/0783* | (2010.01) |
| *A61K 35/17* | (2015.01) |
| *C07K 14/705* | (2006.01) |
| *C07K 14/725* | (2006.01) |
| *C07K 16/30* | (2006.01) |
| *C12N 15/86* | (2006.01) |

(52) U.S. Cl.
CPC ............ *C12N 5/0636* (2013.01); *A61K 35/17* (2013.01); *C07K 14/7051* (2013.01); *C07K 14/70521* (2013.01); *C07K 14/70578* (2013.01); *C07K 16/30* (2013.01); *C12N 15/86* (2013.01); *C07K 2319/02* (2013.01); *C07K 2319/03* (2013.01); *C12N 2510/00* (2013.01); *C12N 2740/15043* (2013.01)

(58) Field of Classification Search
CPC .. C12N 5/0636; C12N 2510/00; A61K 35/17; C07K 14/7051; C07K 14/70578; C07K 16/30

See application file for complete search history.

(56) References Cited

U.S. PATENT DOCUMENTS

2016/0331844 A1* 11/2016 Fotin-Mleczek .... A61K 38/208

FOREIGN PATENT DOCUMENTS

WO WO-2017172981 A2 * 10/2017 ............. A61K 35/17

OTHER PUBLICATIONS

Stowers, Lisa, et al. "Regulation of the polarization of T cells toward antigen-presenting cells by Ras-related GTPase CDC42." Proceedings of the National Academy of Sciences 92.11: 5027-5031. (Year: 1995).*
Tskvitaria-Fuller, Irina, et al. "Specific patterns of Cdc42 activity are related to distinct elements of T cell polarization." The Journal of Immunology 177.3: 1708-1720. (Year: 2006).*
Carpenito, Carmine, et al. "Control of large, established tumor xenografts with genetically retargeted human T cells containing CD28 and CD137 domains." Proceedings of the National Academy of Sciences 106.9: 3360-3365. (Year: 2009).*
Pernis, Alessandra B. "Rho GTPase-mediated pathways in mature CD4+ T cells." Autoimmunity reviews 8.3: 199-203. (Year: 2009).*
Bray, K., Gillette, M., Young, J. et al. Cdc42 overexpression induces hyperbranching in the developing mammary gland by enhancing cell migration. Breast Cancer Res 15, R91. (Year: 2013).*

* cited by examiner

*Primary Examiner* — Arthur S Leonard
*Assistant Examiner* — Josephine M Gonzales
(74) *Attorney, Agent, or Firm* — Lee & Hayes, P.C.

(57) ABSTRACT

Embodiments relate to a modified T cell comprising an antigen binding molecule, wherein expression and/or function of CDC42 in the modified cell has been enhanced. In embodiments, the modified cell has an increased level of cytokine release in response to an antigen that the antigen binding molecule binds as compared to a corresponding T cell that does not overexpress CDC42. In embodiments, the cytokine release comprises a cytokine release of IFNγ. In embodiments, the modified cell has an enhanced migration capability in response to a chemokine as compared to a corresponding T cell that does not overexpress CDC42.

15 Claims, 8 Drawing Sheets

Specification includes a Sequence Listing.

SEQUENCE LISTING

```
<160> NUMBER OF SEQ ID NOS: 47

<210> SEQ ID NO 1
<211> LENGTH: 21
<212> TYPE: PRT
<213> ORGANISM: Homo sapiens

<400> SEQUENCE: 1

Met Ala Leu Pro Val Thr Ala Leu Leu Leu Pro Leu Ala Leu Leu Leu
1               5                   10                  15

His Ala Ala Arg Pro
            20

<210> SEQ ID NO 2
<211> LENGTH: 15
<212> TYPE: PRT
<213> ORGANISM: Artificial Sequence
<220> FEATURE:
<223> OTHER INFORMATION: Synthesized

<400> SEQUENCE: 2

Gly Gly Gly Gly Ser Gly Gly Gly Gly Ser Gly Gly Gly Gly Ser
1               5                   10                  15

<210> SEQ ID NO 3
<211> LENGTH: 42
<212> TYPE: PRT
<213> ORGANISM: Homo sapiens

<400> SEQUENCE: 3

Lys Arg Gly Arg Lys Lys Leu Leu Tyr Ile Phe Lys Gln Pro Phe Met
```

```
                1               5                  10                 15
            Arg Pro Val Gln Thr Thr Gln Glu Glu Asp Gly Cys Ser Cys Arg Phe
                                20                 25                 30

Pro Glu Glu Glu Gly Gly Cys Glu Leu
                    35              40

<210> SEQ ID NO 4
<211> LENGTH: 112
<212> TYPE: PRT
<213> ORGANISM: Artificial Sequence
<220> FEATURE:
<223> OTHER INFORMATION: Synthesized

<400> SEQUENCE: 4

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
        50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 5
<211> LENGTH: 339
<212> TYPE: DNA
<213> ORGANISM: Homo sapiens

<400> SEQUENCE: 5
agagtgaagt tcagcaggag cgcagacgcc cccgcgtacc agcagggcca gaaccagctc      60
tataacgagc tcaatctagg acgaagagag gagtacgatg ttttggacaa gaggcgtggc     120
cgggaccctg agatggggggg aaagccgaga aggaagaacc ctcaggaagg cctgtacaat    180
gaactgcaga aagataagat ggcggaggcc tacagtgaga ttgggatgaa aggcgagcgc     240
cggaggggca aggggcacga tggcctttac cagggtctca gtacagccac caaggacacc    300
tacgacgccc ttcacatgca ggccctgccc cctcgctaa                            339

<210> SEQ ID NO 6
<211> LENGTH: 66
<212> TYPE: PRT
<213> ORGANISM: Artificial Sequence
<220> FEATURE:
<223> OTHER INFORMATION: Synthesized

<400> SEQUENCE: 6

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
```

```
            50                  55                  60

Ile Thr
 65

<210> SEQ ID NO 7
<211> LENGTH: 242
<212> TYPE: PRT
<213> ORGANISM: Artificial Sequence
<220> FEATURE:
<223> OTHER INFORMATION: Synthesized

<400> SEQUENCE: 7

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Lys Tyr
                20                  25                  30

Leu Asn Trp Tyr Gln Gln Lys Pro Gly Lys Ala Pro Lys Leu Leu Ile
             35                  40                  45

Tyr His Thr Ser Arg Leu His Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Asn Thr Leu Pro Tyr
                 85                  90                  95

Thr Phe Gly Gln Gly Thr Lys Val Glu Ile Lys Gly Gly Gly Gly Ser
                100                 105                 110

Gly Gly Gly Gly Ser Gly Gly Gly Ser Glu Val Gln Leu Val Glu
             115                 120                 125

Ser Gly Gly Gly Leu Val Gln Pro Gly Gly Ser Leu Arg Leu Ser Cys
130                 135                 140

Ala Ala Ser Gly Val Ser Leu Pro Asp Tyr Gly Val Ser Trp Val Arg
145                 150                 155                 160

Gln Ala Pro Gly Lys Gly Leu Glu Trp Val Ser Val Ile Trp Gly Ser
                165                 170                 175

Glu Thr Thr Tyr Tyr Asn Ser Ala Leu Lys Ser Arg Phe Thr Ile Ser
            180                 185                 190

Arg Asp Asn Ala Lys Asn Ser Leu Tyr Leu Gln Met Asn Ser Leu Arg
        195                 200                 205

Ala Glu Asp Thr Ala Val Tyr Tyr Cys Ala Lys His Tyr Tyr Tyr Gly
    210                 215                 220

Gly Ser Tyr Ala Met Asp Tyr Trp Gly Gln Gly Thr Leu Val Thr Val
225                 230                 235                 240

Ser Ser

<210> SEQ ID NO 8
<211> LENGTH: 242
<212> TYPE: PRT
<213> ORGANISM: Artificial Sequence
<220> FEATURE:
<223> OTHER INFORMATION: Synthesized

<400> SEQUENCE: 8

Asp Ile Gln Met Thr Gln Thr Thr Ser Ser Leu Ser Ala Ser Leu Gly
 1               5                  10                  15

Asp Arg Val Thr Ile Ser Cys Arg Ala Ser Gln Asp Ile Ser Lys Tyr
                20                  25                  30

Leu Asn Trp Tyr Gln Gln Lys Pro Asp Gly Thr Val Lys Leu Leu Ile
```

```
            35                  40                  45
Tyr His Thr Ser Arg Leu His Ser Gly Val Pro Ser Arg Phe Ser Gly
         50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Gly Asn Thr Leu Pro Tyr
                 85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Ser Glu Val Lys Leu Gln Glu
            115                 120                 125

Ser Gly Pro Gly Leu Val Ala Pro Ser Gln Ser Leu Ser Val Thr Cys
        130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser

<210> SEQ ID NO 9
<211> LENGTH: 237
<212> TYPE: PRT
<213> ORGANISM: Artificial Sequence
<220> FEATURE:
<223> OTHER INFORMATION: Synthesized

<400> SEQUENCE: 9

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Val Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
 65                  70                  75                  80

Glu Asp Phe Gly Ser Tyr Tyr Cys Gln His Phe Trp Gly Thr Pro Tyr
                85                  90                  95

Thr Phe Gly Gly Gly Thr Lys Leu Gly Gly Gly Ser Gly Gly
            100                 105                 110

Gly Ser Gly Gly Gly Gly Ser Glu Val Gln Leu Gln Gln Ser Gly Ala
        115                 120                 125

Glu Leu Val Lys Pro Gly Ala Ser Val Lys Leu Ser Cys Thr Ala Ser
    130                 135                 140

Gly Phe Asn Ile Asn Asp Thr Tyr Met His Trp Val Lys Gln Arg Pro
145                 150                 155                 160
```

Glu Gln Gly Leu Glu Trp Ile Gly Arg Ile Asp Pro Ala Asn Gly Asn
            165                 170                 175

Thr Lys Tyr Asp Pro Lys Phe Gln Gly Lys Ala Thr Ile Thr Ala Asp
        180                 185                 190

Thr Ser Ser Asn Thr Ala Tyr Leu Gln Leu Ser Ser Leu Thr Ser Glu
        195                 200                 205

Asp Thr Ala Val Tyr Tyr Cys Ala Arg Gly Ala Arg Gly Ser Arg Phe
    210                 215                 220

Ala Tyr Trp Gly Gln Gly Thr Leu Val Thr Val Ser Ala
225                 230                 235

<210> SEQ ID NO 10
<211> LENGTH: 244
<212> TYPE: PRT
<213> ORGANISM: Artificial Sequence
<220> FEATURE:
<223> OTHER INFORMATION: Synthesized

<400> SEQUENCE: 10

Gln Ser Val Leu Thr Gln Pro Pro Ser Val Ser Ala Ala Pro Gly Gln
1               5                   10                  15

Lys Val Thr Ile Ser Cys Ser Gly Ser Ser Asp Ile Gly Ser Asn
            20                  25                  30

Tyr Val Ser Trp Tyr Gln Gln Phe Pro Gly Thr Ala Pro Lys Leu Leu
            35                  40                  45

Ile Tyr Asp Asn Asn Lys Arg Pro Ser Ala Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Arg Leu
                85                  90                  95

Gly Ile Ala Val Phe Gly Gly Gly Thr Gln Leu Thr Val Leu Gly Gly
            100                 105                 110

Gly Gly Ser Gly Gly Gly Gly Ser Gly Gly Gly Gly Ser Glu Val Gln
        115                 120                 125

Leu Val Gln Ser Gly Ala Glu Val Lys Lys Pro Gly Gln Ser Leu Lys
    130                 135                 140

Ile Ser Cys Lys Ala Ser Gly Tyr Ser Leu Thr Asp Asn Trp Ile Gly
145                 150                 155                 160

Trp Val Arg Gln Lys Pro Gly Lys Gly Leu Glu Trp Met Gly Ile Ile
                165                 170                 175

Tyr Pro Gly Asp Ser Asp Thr Arg Tyr Ser Pro Ser Phe Gln Gly Gln
            180                 185                 190

Val Thr Ile Ser Ala Asp Lys Ser Ile Asn Thr Ala Tyr Leu Gln Trp
        195                 200                 205

Ser Ser Leu Lys Ala Ser Asp Thr Ala Ile Tyr Tyr Cys Val Gly Leu
    210                 215                 220

Asp Trp Asn Tyr Asn Pro Leu Arg Tyr Trp Gly Pro Gly Thr Leu Val
225                 230                 235                 240

Thr Val Ser Ser

<210> SEQ ID NO 11
<211> LENGTH: 252
<212> TYPE: PRT
<213> ORGANISM: Artificial Sequence
<220> FEATURE:

<223> OTHER INFORMATION: Synthesized

<400> SEQUENCE: 11

```
Asp Ile Val Leu Thr Gln Ser Pro Ala Ser Leu Ala Val Ser Leu Gly
1               5                   10                  15
Gln Gly Ala Thr Ile Ser Cys Arg Ala Ser Lys Ser Val Ser Thr Ser
            20                  25                  30
Gly Tyr Thr Tyr Met His Trp Tyr Gln Gln Lys Pro Gly Gln Pro Pro
        35                  40                  45
Lys Leu Leu Ile Tyr Leu Ala Ser Asn Leu Glu Ser Gly Val Pro Ala
    50                  55                  60
Arg Phe Ser Gly Ser Gly Ser Gly Thr Asp Phe Thr Leu Asn Ile His
65                  70                  75                  80
Pro Val Glu Glu Glu Asp Ala Ala Thr Tyr Tyr Cys Gln His Ser Gly
                85                  90                  95
Glu Leu Pro Pro Ser Phe Gly Gly Gly Thr Lys Leu Glu Ile Lys Arg
            100                 105                 110
Ala Gly Gly Gly Gly Ser Gly Gly Gly Gly Ser Gly Gly Gly Gly Ser
        115                 120                 125
Glu Val Gln Leu Val Glu Ser Gly Gly Asp Leu Val Lys Pro Gly Gly
    130                 135                 140
Ser Leu Lys Leu Ser Cys Ala Val Ser Gly Phe Thr Phe Ser Ser Tyr
145                 150                 155                 160
Gly Met Ser Trp Val Arg Gln Thr Pro Asp Lys Arg Leu Glu Trp Val
                165                 170                 175
Ala Thr Val Ser Ser Gly Gly Thr Tyr Thr Tyr Tyr Pro Asp Ser Val
            180                 185                 190
Lys Gly Arg Phe Thr Ile Ser Arg Asp Asn Ala Lys Asn Thr Leu Tyr
        195                 200                 205
Leu Gln Met Ser Ser Leu Lys Ser Glu Asp Ser Ala Met Tyr Tyr Cys
    210                 215                 220
Ala Arg His Arg Gly Asn Tyr Tyr Ala Thr Tyr Tyr Ala Met Asp
225                 230                 235                 240
Tyr Trp Gly Gln Gly Thr Ser Val Thr Val Ser Ser
                245                 250
```

<210> SEQ ID NO 12
<211> LENGTH: 243
<212> TYPE: PRT
<213> ORGANISM: Artificial Sequence
<220> FEATURE:
<223> OTHER INFORMATION: Synthesized

<400> SEQUENCE: 12

```
Asp Val Gln Ile Thr Gln Ser Pro Ser Tyr Leu Ala Ala Ser Pro Gly
1               5                   10                  15
Glu Thr Ile Thr Ile Asn Cys Arg Ala Ser Lys Ser Ile Ser Lys Tyr
            20                  25                  30
Leu Ala Trp Tyr Gln Glu Lys Pro Gly Lys Thr Asn Lys Leu Leu Ile
        35                  40                  45
Tyr Ser Gly Ser Thr Leu Gln Ser Gly Ile Pro Ser Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Met Tyr Tyr Cys Gln Gln His Asn Glu Tyr Pro Tyr
                85                  90                  95
```

```
Thr Phe Gly Gly Gly Thr Lys Leu Glu Ile Lys Gly Gly Gly Ser
            100                 105                 110

Gly Gly Gly Gly Ser Gly Gly Gly Ser Gln Val Gln Leu Gln Gln
            115                 120                 125

Pro Gly Ala Glu Leu Val Arg Pro Gly Ala Ser Val Lys Leu Ser Cys
            130                 135                 140

Lys Ala Ser Gly Tyr Thr Phe Thr Thr Tyr Trp Met Asn Trp Val Lys
145                 150                 155                 160

Gln Arg Pro Glu Gln Gly Leu Glu Trp Ile Gly Arg Ile Asp Pro Tyr
                165                 170                 175

Asp Ser Glu Thr His Tyr Asn Gln Lys Phe Lys Asp Lys Ala Ile Leu
                180                 185                 190

Thr Val Asp Lys Ser Ser Ser Thr Ala Tyr Met Gln Leu Ser Ser Leu
            195                 200                 205

Thr Ser Glu Asp Ser Ala Val Tyr Tyr Cys Ala Arg Gly Pro Tyr Tyr
            210                 215                 220

Gly Thr Asn Pro Trp Phe Pro Tyr Trp Gly Gln Gly Thr Leu Val Thr
225                 230                 235                 240

Val Ser Ser

<210> SEQ ID NO 13
<211> LENGTH: 241
<212> TYPE: PRT
<213> ORGANISM: Artificial Sequence
<220> FEATURE:
<223> OTHER INFORMATION: Synthesized

<400> SEQUENCE: 13

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Arg Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Gly Ser Leu Gln Ser
65                  70                  75                  80

Glu Asp Phe Ala Val Tyr Tyr Cys Gln Gln Tyr Lys Thr Trp Pro Arg
                85                  90                  95

Thr Phe Gly Gln Gly Thr Asn Val Glu Ile Lys Gly Gly Gly Gly Ser
            100                 105                 110

Gly Gly Gly Gly Ser Gly Gly Gly Ser Gln Val Gln Leu Gln Gln
            115                 120                 125

Trp Gly Ala Gly Leu Leu Lys Pro Ser Glu Thr Leu Ser Leu Thr Cys
            130                 135                 140

Ala Val Phe Gly Gly Ser Phe Ser Gly Tyr Tyr Trp Ser Trp Ile Arg
145                 150                 155                 160

Gln Pro Pro Gly Lys Gly Leu Glu Trp Ile Gly Glu Ile Asn His Arg
                165                 170                 175

Gly Asn Thr Asn Asp Asn Pro Ser Leu Lys Ser Arg Val Thr Ile Ser
            180                 185                 190

Val Asp Thr Ser Lys Asn Gln Phe Ala Leu Lys Leu Ser Ser Val Thr
            195                 200                 205
```

Ala Ala Asp Thr Ala Val Tyr Tyr Cys Ala Arg Glu Arg Gly Tyr Thr
            210                 215                 220
Tyr Gly Asn Phe Asp His Trp Gly Gln Gly Thr Leu Val Thr Val Ser
225                 230                 235                 240

Ser

<210> SEQ ID NO 14
<211> LENGTH: 246
<212> TYPE: PRT
<213> ORGANISM: Artificial Sequence
<220> FEATURE:
<223> OTHER INFORMATION: Synthesized

<400> SEQUENCE: 14

Asp Val Val Met Thr Gln Thr Pro Leu Ser Leu Pro Val Arg Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asn Phe Thr Leu Lys Ile
65                  70                  75                  80

Ser Arg Val Glu Ala Glu Asp Leu Gly Leu Tyr Phe Cys Ser Gln Ser
                85                  90                  95

Thr His Val Pro Tyr Thr Phe Gly Gly Gly Thr Lys Leu Glu Ile Lys
            100                 105                 110

Arg Ala Gly Gly Gly Gly Ser Gly Gly Gly Gly Ser Gly Gly Gly Gly
        115                 120                 125

Ser Gln Val Gln Leu Arg Gln Ser Gly Pro Glu Leu Val Lys Pro Gly
    130                 135                 140

Ala Ser Val Lys Met Ser Cys Lys Ala Ser Gly Tyr Thr Phe Thr Asp
145                 150                 155                 160

Tyr Val Ile Ser Trp Val Lys Gln Arg Thr Gly Gln Gly Leu Glu Trp
                165                 170                 175

Ile Gly Asp Ile Tyr Pro Gly Ser Gly Tyr Ser Phe Tyr Asn Glu Asn
            180                 185                 190

Phe Lys Gly Lys Ala Thr Leu Thr Ala Asp Lys Ser Ser Thr Thr Ala
        195                 200                 205

Tyr Met Gln Leu Ser Ser Leu Thr Ser Glu Asp Ser Ala Val Tyr Phe
    210                 215                 220

Cys Ala Thr Tyr Tyr Asn Tyr Pro Phe Ala Tyr Trp Gly Gln Gly Thr
225                 230                 235                 240

Leu Val Thr Val Ser Ala
            245

<210> SEQ ID NO 15
<211> LENGTH: 199
<212> TYPE: PRT
<213> ORGANISM: Artificial Sequence
<220> FEATURE:
<223> OTHER INFORMATION: Synthesized

<400> SEQUENCE: 15

Leu Pro Ile Cys Pro Gly Gly Ala Ala Arg Cys Gln Val Thr Leu Arg
1               5                   10                  15

Asp Leu Phe Asp Arg Ala Val Val Leu Ser His Tyr Ile His Asn Leu
            20                  25                  30

Ser Ser Glu Met Phe Ser Glu Phe Asp Lys Arg Tyr Thr His Gly Arg
        35                  40                  45

Gly Phe Ile Thr Lys Ala Ile Asn Ser Cys His Thr Ser Ser Leu Ala
    50                  55                  60

Thr Pro Glu Asp Lys Glu Gln Ala Gln Gln Met Asn Gln Lys Asp Phe
65                  70                  75                  80

Leu Ser Leu Ile Val Ser Ile Leu Arg Ser Trp Asn Glu Pro Leu Tyr
                85                  90                  95

His Leu Val Thr Glu Val Arg Gly Met Gln Glu Ala Pro Glu Ala Ile
            100                 105                 110

Leu Ser Lys Ala Val Glu Ile Glu Glu Gln Thr Lys Arg Leu Leu Glu
        115                 120                 125

Gly Met Glu Leu Ile Val Ser Gln Val His Pro Glu Thr Lys Glu Asn
    130                 135                 140

Glu Ile Tyr Pro Val Trp Ser Gly Leu Pro Ser Leu Gln Met Ala Asp
145                 150                 155                 160

Glu Glu Ser Arg Leu Ser Ala Tyr Tyr Asn Leu Leu His Cys Leu Arg
                165                 170                 175

Arg Asp Ser His Lys Ile Asp Asn Tyr Leu Lys Leu Lys Cys Arg
            180                 185                 190

Ile Ile His Asn Asn Asn Cys
        195

<210> SEQ ID NO 16
<211> LENGTH: 240
<212> TYPE: PRT
<213> ORGANISM: Artificial Sequence
<220> FEATURE:
<223> OTHER INFORMATION: Synthesized

<400> SEQUENCE: 16

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Thr Gln
                85                  90                  95

Ser Phe Ile Leu Arg Thr Phe Gly Gln Gly Thr Lys Val Glu Ile Lys
            100                 105                 110

Gly Gly Gly Gly Gly Ser Gly Gly Gly Ser Gly Gly Gly Gly Ser
        115                 120                 125

Asp Ile Val Met Thr Gln Ser Pro Asp Ser Leu Ala Val Ser Leu Gly
    130                 135                 140

Glu Arg Ala Thr Ile Asn Cys Lys Ser Ser Gln Ser Leu Leu Asn Ser
145                 150                 155                 160

Arg Thr Arg Lys Asn Tyr Leu Ala Trp Tyr Gln Gln Lys Pro Gly Gln
                165                 170                 175

```
Pro Pro Lys Leu Leu Ile Tyr Trp Ala Ser Thr Arg Glu Ser Gly Val
            180                 185                 190

Pro Asp Arg Phe Ser Gly Ser Gly Ser Gly Thr Asp Phe Thr Leu Thr
        195                 200                 205

Ile Ser Ser Leu Gln Ala Glu Asp Val Ala Val Tyr Tyr Cys Thr Gln
    210                 215                 220

Ser Phe Ile Leu Arg Thr Phe Gly Gln Gly Thr Lys Val Glu Ile Lys
225                 230                 235                 240

<210> SEQ ID NO 17
<211> LENGTH: 281
<212> TYPE: PRT
<213> ORGANISM: Artificial Sequence
<220> FEATURE:
<223> OTHER INFORMATION: Synthesized

<400> SEQUENCE: 17

Met Asn Val Pro Thr Gln Leu Leu Gly Leu Leu Leu Leu Trp Leu Thr
1               5                   10                  15

Gly Gly Lys Cys Asp Ile Gln Met Thr Gln Ser Pro Ala Ser Leu Ser
            20                  25                  30

Ala Ser Leu Glu Glu Ile Val Thr Ile Thr Cys Lys Ala Ser Gln Ala
        35                  40                  45

Ile Asp Ala Tyr Leu Ser Trp Tyr Gln Gln Lys Pro Gly Lys Ser Pro
    50                  55                  60

Gln Leu Leu Ile Tyr Asp Ala Thr Ser Leu Ala Asp Gly Val Pro Ser
65                  70                  75                  80

Arg Phe Ser Gly Ser Arg Ser Gly Thr Gln Tyr Ser Leu Lys Ile Ser
                85                  90                  95

Arg Pro Gln Val Asp Asp Ser Gly Ile Tyr Tyr Cys Leu Gln Ser Tyr
            100                 105                 110

Ser Thr Pro Phe Thr Phe Gly Ser Gly Thr Lys Leu Glu Ile Lys Gly
        115                 120                 125

Gly Gly Gly Gly Ser Gly Gly Gly Ser Gly Gly Gly Gly Ser Met
        130                 135                 140

Ala Val Leu Val Leu Leu Leu Cys Leu Leu Ile Phe Pro Ser Cys Val
145                 150                 155                 160

Leu Ser Gln Val Gln Leu Lys Glu Ser Gly Pro Gly Leu Val Gln Pro
                165                 170                 175

Ser Gln Thr Leu Ser Leu Thr Cys Thr Val Ser Gly Ser Ser Leu Thr
            180                 185                 190

Ser Asn Ser Val Ser Trp Ile Arg Gln Pro Pro Gly Lys Gly Leu Glu
        195                 200                 205

Trp Met Gly Val Ile Trp Ser Asn Gly Asp Ala Asp Tyr Asn Ser Ala
    210                 215                 220

Ile Lys Ser Arg Leu Ser Ile Ser Arg Asp Thr Ser Lys Ser Gln Val
225                 230                 235                 240

Phe Leu Lys Met Asn Ser Leu Gln Thr Glu Asp Thr Ala Met Tyr Phe
                245                 250                 255

Cys Ala Ser Pro Tyr Tyr Gly Tyr Tyr Phe Pro Phe Asp Tyr Trp Gly
            260                 265                 270

Gln Gly Val Met Val Thr Val Ser Ser
        275                 280

<210> SEQ ID NO 18
<211> LENGTH: 285
```

```
<212> TYPE: PRT
<213> ORGANISM: Artificial Sequence
<220> FEATURE:
<223> OTHER INFORMATION: Synthesized

<400> SEQUENCE: 18

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Leu Ala Val
            20                  25                  30

Ser Leu Gly Gln Arg Ala Thr Ile Ser Cys Arg Ala Ser Gln Ser Val
        35                  40                  45

Ser Ile Ser Ser His Asp Leu Met Gln Trp Tyr Gln Gln Lys Pro Gly
    50                  55                  60

Gln Gln Pro Lys Leu Leu Ile Tyr Asp Ala Phe Asn Leu Ala Ser Gly
65                  70                  75                  80

Ile Pro Val Arg Phe Ser Gly Ser Gly Ser Gly Thr Asp Phe Thr Leu
                85                  90                  95

Thr Ile Asp Pro Val Gln Ala Asp Asp Ile Ala Thr Tyr Tyr Cys Gln
            100                 105                 110

Gln Ser Lys Asp Pro Tyr Thr Phe Gly Ala Gly Thr Lys Leu Glu
        115                 120                 125

Leu Lys Gly Gly Gly Gly Ser Gly Gly Gly Ser Gly Gly Gly
    130                 135                 140

Gly Ser Met Asp Ile Arg Leu Ser Leu Ala Phe Leu Val Leu Phe Ile
145                 150                 155                 160

Lys Gly Val Gln Cys Glu Val Gln Leu Val Glu Ser Gly Gly Gly Leu
                165                 170                 175

Val Gln Pro Gly Arg Ser Met Lys Leu Ser Cys Ala Ala Ser Gly Phe
            180                 185                 190

Thr Phe Ser Asn Tyr Gly Met Ala Trp Val Arg Gln Ala Pro Thr Lys
        195                 200                 205

Gly Leu Glu Trp Val Ala Thr Ile Ser Tyr Asp Gly Ser Ile Thr Tyr
    210                 215                 220

Tyr Arg Asp Ser Val Lys Gly Arg Phe Thr Ile Ser Arg Asp His Ala
225                 230                 235                 240

Lys Ser Thr Leu Tyr Leu Gln Met Asn Ser Leu Arg Ser Glu Asp Thr
                245                 250                 255

Ala Thr Tyr Tyr Cys Thr Arg Glu Glu Gln Tyr Ser Ser Trp Tyr Phe
            260                 265                 270

Asp Phe Trp Gly Pro Gly Ile Met Val Thr Val Ser Ser
        275                 280                 285

<210> SEQ ID NO 19
<211> LENGTH: 242
<212> TYPE: PRT
<213> ORGANISM: Artificial Sequence
<220> FEATURE:
<223> OTHER INFORMATION: Synthesized

<400> SEQUENCE: 19

Asn Ile Val Met Thr Gln Ser Pro Ser Ser Leu Ser Ala Ser Val Gly
1               5                   10                  15

Asp Arg Val Thr Ile Thr Cys Gln Ala Ser Gln Asp Val Gly Thr Ala
            20                  25                  30

Val Ala Trp Tyr Gln Gln Lys Pro Asp Gln Ser Pro Lys Leu Leu Ile
        35                  40                  45
```

```
Tyr Trp Thr Ser Thr Arg His Thr Gly Val Pro Asp Arg Phe Thr Gly
            50                  55                  60

Ser Gly Ser Gly Thr Asp Phe Thr Leu Thr Ile Ser Ser Leu Gln Pro
 65                  70                  75                  80

Glu Asp Ile Ala Thr Tyr Phe Cys His Gln Tyr Asn Ser Tyr Asn Thr
                 85                  90                  95

Phe Gly Ser Gly Thr Lys Leu Glu Ile Lys Gly Gly Gly Gly Gly Ser
            100                 105                 110

Gly Gly Gly Gly Ser Gly Gly Gly Ser Gln Val Thr Leu Lys Glu
            115                 120                 125

Ser Gly Pro Val Leu Val Lys Pro Thr Glu Thr Leu Thr Leu Thr Cys
130                 135                 140

Thr Phe Ser Gly Phe Ser Leu Ser Thr Ser Gly Met Gly Val Gly Trp
145                 150                 155                 160

Ile Arg Gln Ala Pro Gly Lys Gly Leu Glu Trp Val Ala His Ile Trp
                165                 170                 175

Trp Asp Asp Asp Val Tyr Tyr Asn Pro Ser Leu Lys Ser Arg Leu Thr
                180                 185                 190

Ile Thr Lys Asp Ala Ser Lys Asp Gln Val Ser Leu Lys Leu Ser Ser
            195                 200                 205

Val Thr Ala Ala Asp Thr Ala Val Tyr Tyr Cys Val Arg Arg Arg Ala
210                 215                 220

Thr Gly Thr Gly Phe Asp Tyr Trp Gly Gln Gly Thr Leu Val Thr Val
225                 230                 235                 240

Ser Ser

<210> SEQ ID NO 20
<211> LENGTH: 244
<212> TYPE: PRT
<213> ORGANISM: Artificial Sequence
<220> FEATURE:
<223> OTHER INFORMATION: Synthesized

<400> SEQUENCE: 20

Asp Ile Val Met Thr Gln Ser Pro Ser Ser Leu Thr Val Thr Ala Gly
  1               5                  10                  15

Glu Lys Val Thr Met Ile Cys Lys Ser Ser Gln Ser Leu Leu Asn Ser
                 20                  25                  30

Gly Asp Gln Lys Asn Tyr Leu Thr Trp Tyr Gln Gln Lys Pro Gly Gln
             35                  40                  45

Pro Pro Lys Leu Leu Ile Phe Trp Ala Ser Thr Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Gln Asn
                 85                  90                  95

Asp Tyr Ser Tyr Pro Leu Thr Phe Gly Ala Gly Thr Lys Leu Glu Leu
            100                 105                 110

Lys Gly Gly Gly Gly Ser Gly Gly Gly Gly Ser Gly Gly Gly Gly Ser
            115                 120                 125

Gln Val Gln Leu Gln Gln Ser Asp Ala Glu Leu Val Lys Pro Gly Ser
            130                 135                 140

Ser Val Lys Ile Ser Cys Lys Ala Ser Gly Tyr Thr Phe Thr Asp His
145                 150                 155                 160
```

Ala Ile His Trp Val Lys Gln Lys Pro Glu Gln Gly Leu Glu Trp Ile
              165                 170                 175

Gly His Phe Ser Pro Gly Asn Thr Asp Ile Lys Tyr Asn Asp Lys Phe
          180                 185                 190

Lys Gly Lys Ala Thr Leu Thr Val Asp Arg Ser Ser Ser Thr Ala Tyr
      195                 200                 205

Met Gln Leu Asn Ser Leu Thr Ser Glu Asp Ser Ala Val Tyr Phe Cys
  210                 215                 220

Lys Thr Ser Thr Phe Phe Asp Tyr Trp Gly Gln Gly Thr Thr Leu
225                 230                 235                 240

Thr Val Ser Ser

<210> SEQ ID NO 21
<211> LENGTH: 246
<212> TYPE: PRT
<213> ORGANISM: Artificial Sequence
<220> FEATURE:
<223> OTHER INFORMATION: Synthesized

<400> SEQUENCE: 21

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Phe Phe Trp Tyr Leu Gln Lys Pro Gly Leu Ser
        35                  40                  45

Pro Gln Leu Leu Ile Tyr Gln Met Ser Asn Leu Ala Ser Gly Val Pro
    50                  55                  60

Asp Arg Phe Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Pro Thr Phe Gly Gly Gly Thr Lys Leu Glu Ile Lys
            100                 105                 110

Arg Ala Gly Gly Gly Gly Ser Gly Gly Gly Ser Gly Gly Gly Gly
        115                 120                 125

Ser Glu Val Lys Leu Val Glu Ser Gly Gly Gly Leu Val Gln Pro Gly
    130                 135                 140

Gly Ser Met Lys Leu Ser Cys Val Ala Ser Gly Phe Thr Phe Ser Asn
145                 150                 155                 160

Tyr Trp Met Asn Trp Val Arg Gln Ser Pro Glu Lys Gly Leu Glu Trp
                165                 170                 175

Val Ala Glu Ile Arg Leu Lys Ser Asn Asn Tyr Thr Thr His Tyr Ala
            180                 185                 190

Glu Ser Val Lys Gly Arg Phe Thr Ile Ser Arg Asp Asp Ser Lys Ser
        195                 200                 205

Ser Val Ser Leu Gln Met Asn Asn Leu Arg Val Glu Asp Thr Gly Ile
    210                 215                 220

Tyr Tyr Cys Thr Arg His Tyr Tyr Phe Asp Tyr Trp Gly Gln Gly Thr
225                 230                 235                 240

Thr Leu Thr Val Ser Ser
                245

<210> SEQ ID NO 22
<211> LENGTH: 2291
<212> TYPE: DNA

<213> ORGANISM: Homo sapiens

<400> SEQUENCE: 22

```
tggcgacgcc gggaagcgaa ccccaacctt tcgtcccggc cctttcggta gctactctgc      60
acccacttca tcatccccac caccaccacc accaccatca gcaccacgga ggaaccggcg     120
cccccggcgg ggcgggtggt ggcggcggtg gcagcggggg cttcaacctg cccttgaacc     180
ggggtctgga gcgcgcgctt gaggaggcgg ccaactccgg ggggctgaac ctgagcgcca     240
ggaaattgaa ggaatttccc cgtaccgcag cccccgggca cgacctctcg gacacggtgc     300
aggcagactt atctaaaaac agactggttg aagttccaat ggaattgtgc cattttgtat     360
cactggaaat tcttaatctg tatcacaact gtatcagagt cattcctgag gccatcgtta     420
atctgcagat gctgacttac ctgaacttga gtcgaaatca gctgtccgcc ctgcctgcct     480
gcctgtgtgg tctgcctctc aaagtcttaa tcgcaagtaa caacaaactt ggatcattac     540
cagaagagat aggtcagctc aaacagttaa tggagctgga tgtcagctgc aacgagatca     600
cagcgttgcc ccagcagata ggtcagttga atctctacg agaactgaat gtcagaagaa     660
attaccttaa agttttacca caagaactag tagatcttcc cttggtaaag tttgactttt     720
cctgcaacaa agtgctcgtg attccaattt gttttagaga gatgaagcag ctgcaagtgt     780
tactacttga gataaaccct ctgcagtctc ctccagcaca gatttgcaca aagggcaaag     840
ttcacatatt taagtatctg agcatacaag catgccagat taagacagct gactcccttt     900
atctccacac catggagagg ccacatttac accagcacgt ggaagatggc aagaaggatt     960
ctgattcggg agttggaagt gataatggag ataagcgatt atctgccacc gagccttctg    1020
acgaagacac tgttagcctc aatgtgccaa tgtcaaacat catggaagaa gaacagatca    1080
tcaaggagga ctcgtgccat cgccttagcc ccgttaaagg ggaatttcat caggaatttc    1140
aaccggagcc ttcccttttg ggtgacagca ccaactcagg agaagaaaga gaccagttta    1200
ctgatagagc agatggtctc cattcggaat ttatgaacta taaggcaagg gcagaagact    1260
gtgaagagct gttacggata aagaggatg tgcactggca aactgagggc ataataagtt    1320
catccaaaga tcaggacatg gatatagcaa tgatcgagca gctgagagaa gcagtagatt    1380
tgctgcaaga tcccaatgga ttaagcacag atattacaga gagaagtgtt ttaaacctat    1440
atcctatggg atcagcagaa gccttagaat tacaagattc tgcactgaat ggtcaaatac    1500
agctggagac atctccggtg tgtgaggtgc aaagtgatct aacattacag agtaacggga    1560
gccagtattc tccaaatgag attagagaga actcccctgc agtctctcct accacaaaca    1620
gcacagctcc atttggcctg aagcctcgat cagacccagc cctcattctt cctcctatct    1680
ccttcaacac acttacacag gcacagacat gggacagctc tagctacagt gttccatctg    1740
aaggagacag tgacaatgtg tttctaagac ctcagagaaa tttggaatct atagacccgc    1800
agtttacaat ccggaggaaa atggagcaga tgagagaaga gaaagagctg gtggaacaac    1860
ttcgtgagag cattgagatg agattgaagg tcagtctaca cgaagacctg ggggcagccc    1920
tcatggatgg tgtcgtcctc tgccatctgg tcaaccacat ccgcccacgg tcggttgcaa    1980
gcatccatgt cccatcacca gcggttccca aacttagcat ggccaaatgc agaagaaatg    2040
tggaaaactt tttggaagcg tgccgaaaat taggagtacc agaggctgac ctctgctctc    2100
cgtgtgacat cctgcagttg gattttcgtc acattcgaaa gactgttgac actctgctgg    2160
cactcgggga gaaagcccca ccaccaactt ctgccctccg ctccagggac cttataggct    2220
tctgtcttgt ccatattctc tttatagtgc tggtctatat cacttaccac tggaatgctc    2280
```
tgtccgcata a    2291

<210> SEQ ID NO 23
<211> LENGTH: 30
<212> TYPE: DNA
<213> ORGANISM: Homo sapiens

<400> SEQUENCE: 23
atggcgacgc cgggaagcga accccaacct    30

<210> SEQ ID NO 24
<211> LENGTH: 52
<212> TYPE: DNA
<213> ORGANISM: Homo sapiens

<400> SEQUENCE: 24
tcgtcccggc cctttcggta gctactctgc acccacttca tcatcccac ca    52

<210> SEQ ID NO 25
<211> LENGTH: 23
<212> TYPE: DNA
<213> ORGANISM: Homo sapiens

<400> SEQUENCE: 25
tgaggaggcg gccaactccg ggg    23

<210> SEQ ID NO 26
<211> LENGTH: 7
<212> TYPE: PRT
<213> ORGANISM: Artificial Sequence
<220> FEATURE:
<223> OTHER INFORMATION: Synthesized

<400> SEQUENCE: 26

Thr Ser Gly Asn Leu Thr Glu
1               5

<210> SEQ ID NO 27
<211> LENGTH: 7
<212> TYPE: PRT
<213> ORGANISM: Artificial Sequence
<220> FEATURE:
<223> OTHER INFORMATION: Synthesized

<400> SEQUENCE: 27

His Thr Gly His Leu Leu Glu
1               5

<210> SEQ ID NO 28
<211> LENGTH: 7
<212> TYPE: PRT
<213> ORGANISM: Artificial Sequence
<220> FEATURE:
<223> OTHER INFORMATION: Synthesized

<400> SEQUENCE: 28

Ser Arg Arg Thr Cys Arg Ala
1               5

<210> SEQ ID NO 29
<211> LENGTH: 7
<212> TYPE: PRT
<213> ORGANISM: Artificial Sequence
<220> FEATURE:
<223> OTHER INFORMATION: Synthesized

<400> SEQUENCE: 29

Arg Ser Asp Lys Leu Thr Glu
1               5

<210> SEQ ID NO 30
<211> LENGTH: 7
<212> TYPE: PRT
<213> ORGANISM: Artificial Sequence
<220> FEATURE:
<223> OTHER INFORMATION: Synthesized

<400> SEQUENCE: 30

Thr Lys Asn Ser Leu Thr Glu
1               5

<210> SEQ ID NO 31
<211> LENGTH: 7
<212> TYPE: PRT
<213> ORGANISM: Artificial Sequence
<220> FEATURE:
<223> OTHER INFORMATION: Synthesized

<400> SEQUENCE: 31

Gln Ser Gly Asn Leu Thr Glu
1               5

<210> SEQ ID NO 32
<211> LENGTH: 7
<212> TYPE: PRT
<213> ORGANISM: Artificial Sequence
<220> FEATURE:
<223> OTHER INFORMATION: Synthesized

<400> SEQUENCE: 32

Ser Lys Lys His Leu Ala Glu
1               5

<210> SEQ ID NO 33
<211> LENGTH: 7
<212> TYPE: PRT
<213> ORGANISM: Artificial Sequence
<220> FEATURE:
<223> OTHER INFORMATION: Synthesized

<400> SEQUENCE: 33

Gln Ser Ser Asn Leu Val Arg
1               5

<210> SEQ ID NO 34
<211> LENGTH: 18
<212> TYPE: DNA
<213> ORGANISM: Artificial Sequence
<220> FEATURE:
<223> OTHER INFORMATION: Synthesized

<400> SEQUENCE: 34
tcgtcccggc cctttcgg                                                 18

<210> SEQ ID NO 35
<211> LENGTH: 18
<212> TYPE: DNA
<213> ORGANISM: Artificial Sequence
<220> FEATURE:
<223> OTHER INFORMATION: Synthesized

<400> SEQUENCE: 35
acttcatcat ccccacca                                                         18

<210> SEQ ID NO 36
<211> LENGTH: 16
<212> TYPE: DNA
<213> ORGANISM: Artificial Sequence
<220> FEATURE:
<223> OTHER INFORMATION: Synthesized

<400> SEQUENCE: 36
tagctactct gcaccc                                                           16

<210> SEQ ID NO 37
<211> LENGTH: 48
<212> TYPE: DNA
<213> ORGANISM: Artificial Sequence
<220> FEATURE:
<223> OTHER INFORMATION: Synthesized

<400> SEQUENCE: 37
gccggcagct agcgacgcca tctcgagatg gcgtcgctag ctgccggc                        48

<210> SEQ ID NO 38
<211> LENGTH: 48
<212> TYPE: DNA
<213> ORGANISM: Artificial Sequence
<220> FEATURE:
<223> OTHER INFORMATION: Synthesized

<400> SEQUENCE: 38
gaccttatag gcttctgtct tctcgagaag acagaagcct ataaggtc                        48

<210> SEQ ID NO 39
<211> LENGTH: 723
<212> TYPE: DNA
<213> ORGANISM: Artificial Sequence
<220> FEATURE:
<223> OTHER INFORMATION: Synthesized

<400> SEQUENCE: 39
gagatcgtga tgacccagtc ccctgccaca ctgtccgtgt ctccaggaga gagggccacc           60
ctgtcttgca gggctagcca gtccgtgtct aggaacctgg cctggtacca gcagaagcca          120
ggccaggctc ccagactgct gatctacgga gcttccacca gggctacagg aatcccagct          180
agattcagcg gctccggatc tggcaccgag tttaccctga caatcggctc tctgcagagc          240
gaggacttcg ccgtgtacta ctgccagcag tacaagacct ggcctcggac atttggacag          300
ggcacaaacg tggagatcaa gggaggagga ggatccggag gaggaggatc tggaggagga          360
ggaagccagg tgcagctgca gcagtgggga gctggcctgc tgaagccaag cgagacactg          420
tccctgacat gtgccgtgtt cggcggaagc ttttccggct actactggag ctggatcagg          480 cagcccctg gaaagggcct ggagtggatc ggagagatca ccaccggggg caacaccaac           540
gacaacccct ccctgaagtc tcgcgtgacc atctctgtgg atacaagcaa gaaccagttc          600
gccctgaagc tgagctccgt gaccgctgct gacacagccg tgtactactg tgctagggag          660
agaggataca catacggcaa ctttgatcac tggggacagg gcaccctggt gacagtgtct          720
agc                                                                        723

<210> SEQ ID NO 40
<211> LENGTH: 22
<212> TYPE: PRT

```
<213> ORGANISM: Artificial Sequence
<220> FEATURE:
<223> OTHER INFORMATION: Synthesized

<400> SEQUENCE: 40

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 41
<211> LENGTH: 69
<212> TYPE: PRT
<213> ORGANISM: Artificial Sequence
<220> FEATURE:
<223> OTHER INFORMATION: Synthesized

<400> SEQUENCE: 41

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65

<210> SEQ ID NO 42
<211> LENGTH: 576
<212> TYPE: DNA
<213> ORGANISM: Artificial Sequence
<220> FEATURE:
<223> OTHER INFORMATION: Synthesized

<400> SEQUENCE: 42
atgcagacca tcaagtgtgt ggtggtcgga gacggagccg tgggaaagac atgcctcctc      60
atctcctaca ccaccaacaa gttccccagc gagtacgtgc ccaccgtgtt tgacaactac     120
gccgtgaccg tgatgatcgg cggagagccc tacacactgg gactgttcga caccgccgga     180
caagaggatt acgatagact gagacctctg tcctatcctc agaccgatgt ctttctggtg     240
tgctttagcg tggtgagccc ctcctccttc gagaacgtga agagaagtgg gtccccgag      300
atcacccacc actgccccaa acccccttt ctgctggtgg caccagat tgatctgagg        360
gatgaccca gcaccatcga gaagctcgcc aagaacaagc agaagcccat taccccgag       420
accgctgaga agctggctag agatctgaag gccgtcaagt acgtggagtg cagcgctctg     480
acccagaagg gactgaagaa tgtgttcgac gaagccattc tggccgctct ggagcctccc     540
gagcccaaaa agagcagaag gtgcgtgctg ctgtga                              576

<210> SEQ ID NO 43
<211> LENGTH: 191
<212> TYPE: PRT
<213> ORGANISM: Artificial Sequence
<220> FEATURE:
<223> OTHER INFORMATION: Synthesized

<400> SEQUENCE: 43

Met Gln Thr Ile Lys Cys Val Val Val Gly Asp Gly Ala Val Gly Lys
1               5                   10                  15
```

```
Thr Cys Leu Leu Ile Ser Tyr Thr Thr Asn Lys Phe Pro Ser Glu Tyr
            20                  25                  30

Val Pro Thr Val Phe Asp Asn Tyr Ala Val Thr Val Met Ile Gly Gly
        35                  40                  45

Glu Pro Tyr Thr Leu Gly Leu Phe Asp Thr Ala Gly Gln Glu Asp Tyr
    50                  55                  60

Asp Arg Leu Arg Pro Leu Ser Tyr Pro Gln Thr Asp Val Phe Leu Val
65                  70                  75                  80

Cys Phe Ser Val Val Ser Pro Ser Ser Phe Glu Asn Val Lys Glu Lys
                85                  90                  95

Trp Val Pro Glu Ile Thr His His Cys Pro Lys Thr Pro Phe Leu Leu
            100                 105                 110

Val Gly Thr Gln Ile Asp Leu Arg Asp Asp Pro Ser Thr Ile Glu Lys
        115                 120                 125

Leu Ala Lys Asn Lys Gln Lys Pro Ile Thr Pro Glu Thr Ala Glu Lys
    130                 135                 140

Leu Ala Arg Asp Leu Lys Ala Val Lys Tyr Val Glu Cys Ser Ala Leu
145                 150                 155                 160

Thr Gln Lys Gly Leu Lys Asn Val Phe Asp Glu Ala Ile Leu Ala Ala
                165                 170                 175

Leu Glu Pro Pro Glu Pro Lys Lys Ser Arg Arg Cys Val Leu Leu
            180                 185                 190

<210> SEQ ID NO 44
<211> LENGTH: 2097
<212> TYPE: DNA
<213> ORGANISM: Artificial Sequence
<220> FEATURE:
<223> OTHER INFORMATION: Synthesized

<400> SEQUENCE: 44
atggccttac cagtgaccgc cttgctcctg ccgctggcct tgctgctcca cgccgccagg      60
ccggagatcg tgatgaccca gtcccctgcc acactgtccg tgtctccagg agagagggcc    120
accctgtctt gcagggctag ccagtccgtg tctaggaacc tggcctggta ccagcagaag    180
ccaggccagg ctcccagact gctgatctac ggagcttcca ccagggctac aggaatccca    240
gctagattca gcggctccgg atctggcacc gagtttaccc tgacaatcgg ctctctgcag    300
agcgaggact cgccgtgta ctactgccag cagtacaaga cctggcctcg acatttgga    360 cagggcacaa acgtggagat caaggagga ggaggatccg gaggaggagg atctggagga    420
ggaggaagcc aggtgcagct gcagcagtgg ggagctggcc tgctgaagcc aagcgagaca    480
ctgtccctga catgtgccgt gttcggcgga agcttttccg ctactactg agctggatc     540 aggcagcccc ctggaaaggg cctggagtgg atcggagaga tcaaccaccg gggcaacacc    600
aacgacaacc cctccctgaa gtctcgcgtg accatctctg tggatacaag caagaaccag    660
ttcgccctga agctgagctc cgtgaccgct gctgacacag ccgtgtacta ctgtgctagg    720
gagagaggat acacatacgg caactttgat cactggggac agggcaccct ggtgacagtg    780
tctagcacca cgacgccagc gccgcgacca ccaacaccgg cgccaccat cgcgtcgcag    840 cccctgtccc tgcgcccaga ggtgccgg ccagcggcgg ggggcgcagt gcacacgagg    900
gggctggact cgcctgtga tatctacatc tgggcgccct tggccgggac ttgtggggtc    960
cttctcctgt cactggttat caccctttac tgcaaacggg gcagaaagaa actcctgtat   1020
atattcaaac aaccatttat gagaccagta caaactactc aagaggaaga tggctgtagc   1080
```

```
tgccgatttc agaagaaga agaaggagga tgtgaactga gagtgaagtt cagcaggagc    1140
gcagacgccc ccgcgtacca gcagggccag aaccagctct ataacgagct caatctagga    1200
cgaagagagg agtacgatgt tttggacaag aggcgtggcc gggaccctga tggggggga    1260 aagccgagaa ggaagaaccc tcaggaaggc ctgtacaatg aactgcagaa agataagatg    1320
gcggaggcct acagtgagat tgggatgaaa ggcgagcgcc ggaggggcaa ggggcacgat    1380
ggcctttacc agggtctcag tacagccacc aaggacacct acgacgccct tcacatgcag    1440
gccctgcccc ctcgcggttc cggagccacg aacttctctc tgttaaagca agcaggagac    1500
gtggaagaaa accccggtcc tatgcagacc atcaagtgtg tggtggtcgg agacggagcc    1560
gtgggaaaga catgcctcct catctcctac accaccaaca agttccccag cgagtacgtg    1620
cccaccgtgt ttgacaacta cgccgtgacc gtgatgatcg gcggagagcc ctacacactg    1680
ggactgttcg acaccgccgg acaagaggat tacgatagac tgagacctct gtcctatcct    1740
cagaccgatg tctttctggt gtgctttagc gtggtgagcc cctcctcctt cgagaacgtg    1800
aaagagaagt gggtccccga gatcacccac cactgcccca aaaccccctt tctgctggtg    1860
ggcacccaga ttgatctgag ggatgacccc agcaccatcg agaagctcgc caagaacaag    1920
cagaagccca ttaccccccga gaccgctgag aagctggcta gagatctgaa ggccgtcaag    1980
tacgtggagt gcagcgctct gacccagaag ggactgaaga atgtgttcga cgaagccatt    2040
ctggccgctc tggagcctcc cgagcccaaa aagagcagaa ggtgcgtgct gctgtga       2097
```

<210> SEQ ID NO 45
<211> LENGTH: 698
<212> TYPE: PRT
<213> ORGANISM: Artificial Sequence
<220> FEATURE:
<223> OTHER INFORMATION: Synthesized

<400> SEQUENCE: 45

```
Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
                20                  25                  30

Ser Val Ser Pro Gly Glu Arg Ala Thr Leu Ser Cys Arg Ala Ser Gln
            35                  40                  45

Ser Val Ser Arg Asn Leu Ala Trp Tyr Gln Gln Lys Pro Gly Gln Ala
        50                  55                  60

Pro Arg Leu Leu Ile Tyr Gly Ala Ser Thr Arg Ala Thr Gly Ile Pro
65                  70                  75                  80

Ala Arg Phe Ser Gly Ser Gly Ser Gly Thr Glu Phe Thr Leu Thr Ile
                85                  90                  95

Gly Ser Leu Gln Ser Glu Asp Phe Ala Val Tyr Tyr Cys Gln Gln Tyr
                100                 105                 110

Lys Thr Trp Pro Arg Thr Phe Gly Gln Gly Thr Asn Val Glu Ile Lys
            115                 120                 125

Gly Gly Gly Gly Ser Gly Gly Gly Ser Gly Gly Gly Ser Gln
        130                 135                 140

Val Gln Leu Gln Gln Trp Gly Ala Gly Leu Leu Lys Pro Ser Glu Thr
145                 150                 155                 160

Leu Ser Leu Thr Cys Ala Val Phe Gly Gly Ser Phe Ser Gly Tyr Tyr
                165                 170                 175

Trp Ser Trp Ile Arg Gln Pro Pro Gly Lys Gly Leu Glu Trp Ile Gly
```

-continued

```
                180                 185                 190
Glu Ile Asn His Arg Gly Asn Thr Asn Asp Asn Pro Ser Leu Lys Ser
            195                 200                 205
Arg Val Thr Ile Ser Val Asp Thr Ser Lys Asn Gln Phe Ala Leu Lys
        210                 215                 220
Leu Ser Ser Val Thr Ala Ala Asp Thr Ala Val Tyr Tyr Cys Ala Arg
225                 230                 235                 240
Glu Arg Gly Tyr Thr Tyr Gly Asn Phe Asp His Trp Gly Gln Gly Thr
                245                 250                 255
Leu Val Thr Val Ser Ser Thr Thr Thr Pro Ala Pro Arg Pro Pro Thr
            260                 265                 270
Pro Ala Pro Thr Ile Ala Ser Gln Pro Leu Ser Leu Arg Pro Glu Ala
        275                 280                 285
Cys Arg Pro Ala Ala Gly Gly Ala Val His Thr Arg Gly Leu Asp Phe
            290                 295                 300
Ala Cys Asp Ile Tyr Ile Trp Ala Pro Leu Ala Gly Thr Cys Gly Val
305                 310                 315                 320
Leu Leu Leu Ser Leu Val Ile Thr Leu Tyr Cys Lys Arg Gly Arg Lys
                325                 330                 335
Lys Leu Leu Tyr Ile Phe Lys Gln Pro Phe Met Arg Pro Val Gln Thr
            340                 345                 350
Thr Gln Glu Glu Asp Gly Cys Ser Cys Arg Phe Pro Glu Glu Glu Glu
        355                 360                 365
Gly Gly Cys Glu Leu Arg Val Lys Phe Ser Arg Ser Ala Asp Ala Pro
            370                 375                 380
Ala Tyr Gln Gln Gly Gln Asn Gln Leu Tyr Asn Glu Leu Asn Leu Gly
385                 390                 395                 400
Arg Arg Glu Glu Tyr Asp Val Leu Asp Lys Arg Arg Gly Arg Asp Pro
                405                 410                 415
Glu Met Gly Gly Lys Pro Arg Arg Lys Asn Pro Gln Glu Gly Leu Tyr
            420                 425                 430
Asn Glu Leu Gln Lys Asp Lys Met Ala Glu Ala Tyr Ser Glu Ile Gly
        435                 440                 445
Met Lys Gly Glu Arg Arg Arg Gly Lys Gly His Asp Gly Leu Tyr Gln
    450                 455                 460
Gly Leu Ser Thr Ala Thr Lys Asp Thr Tyr Asp Ala Leu His Met Gln
465                 470                 475                 480
Ala Leu Pro Pro Arg Gly Ser Gly Ala Thr Asn Phe Ser Leu Leu Lys
                485                 490                 495
Gln Ala Gly Asp Val Glu Glu Asn Pro Gly Pro Met Gln Thr Ile Lys
            500                 505                 510
Cys Val Val Val Gly Asp Gly Ala Val Gly Lys Thr Cys Leu Leu Ile
        515                 520                 525
Ser Tyr Thr Thr Asn Lys Phe Pro Ser Glu Tyr Val Pro Thr Val Phe
    530                 535                 540
Asp Asn Tyr Ala Val Thr Val Met Ile Gly Gly Glu Pro Tyr Thr Leu
545                 550                 555                 560
Gly Leu Phe Asp Thr Ala Gly Gln Glu Asp Tyr Asp Arg Leu Arg Pro
                565                 570                 575
Leu Ser Tyr Pro Gln Thr Asp Val Phe Leu Val Cys Phe Ser Val Val
            580                 585                 590
Ser Pro Ser Ser Phe Glu Asn Val Lys Glu Lys Trp Val Pro Glu Ile
        595                 600                 605
```

```
Thr His His Cys Pro Lys Thr Pro Phe Leu Leu Val Gly Thr Gln Ile
    610                 615                 620
Asp Leu Arg Asp Asp Pro Ser Thr Ile Glu Lys Leu Ala Lys Asn Lys
625                 630                 635                 640
Gln Lys Pro Ile Thr Pro Glu Thr Ala Glu Lys Leu Ala Arg Asp Leu
                645                 650                 655
Lys Ala Val Lys Tyr Val Glu Cys Ser Ala Leu Thr Gln Lys Gly Leu
            660                 665                 670
Lys Asn Val Phe Asp Glu Ala Ile Leu Ala Ala Leu Glu Pro Pro Glu
        675                 680                 685
Pro Lys Lys Ser Arg Arg Cys Val Leu Leu
    690                 695

<210> SEQ ID NO 46
<211> LENGTH: 1458
<212> TYPE: DNA
<213> ORGANISM: Artificial Sequence
<220> FEATURE:
<223> OTHER INFORMATION: Synthesized

<400> SEQUENCE: 46
atggccttac cagtgaccgc cttgctcctg ccgctggcct tgctgctcca cgccgccagg      60
ccggagatcg tgatgaccca gtcccctgcc acactgtccg tgtctccagg agagagggcc    120
accctgtctt gcagggctag ccagtccgtg tctaggaacc tggcctggta ccagcagaag    180
ccaggccagg ctcccagact gctgatctac ggagcttcca ccagggctac aggaatccca    240
gctagattca gcggctccgg atctggcacc gagtttaccc tgacaatcgg ctctctgcag    300
agcgaggact cgccgtgta ctactgccag cagtacaaga cctggcctcg gacatttgga    360
cagggcacaa cgtggagat caaggagga ggaggatccg gaggaggagg atctggagga    420
ggaggaagcc aggtgcagct gcagcagtgg ggagctggcc tgctgaagcc aagcgagaca    480
ctgtccctga catgtgccgt gttcggcgga agcttttccg gctactactg gagctggatc    540
aggcagcccc ctggaaaggg cctggagtgg atcggagaga tcaaccaccg gggcaacacc    600
aacgacaacc cctccctgaa gtctcgcgtg accatctctg tggatacaag caagaaccag    660
ttcgccctga agctgagctc cgtgaccgct gctgacacag ccgtgtacta ctgtgctagg    720
gagagaggat acacatacgg caactttgat cactggggac agggcaccct ggtgacagtg    780
tctagcacca cgacgccagc gccgcgacca ccaacaccgg cgcccaccat cgcgtcgcag    840 ccccctgtccc tgcgcccaga ggcgtgccgg ccagcggcgg gggcgcagt gcacacgagg    900 gggctggact cgccctgtga tatctacatc tgggcgccct tggccgggac ttgtggggtc    960
cttctcctgt cactggttat cacccttttac tgcaaacggg gcagaaagaa actcctgtat   1020
atattcaaac aaccatttat gagaccagta caaactactc aagaggaaga tggctgtagc   1080
tgccgatttc cagaagaaga agaaggagga tgtgaactga gagtgaagtt cagcaggagc   1140
gcagacgccc ccgcgtacca gcagggccag aaccagctct ataacgagct caatctagga   1200
cgaagagagg agtacgatgt tttggacaag aggcgtggcc gggaccctga tgggggga    1260 aagccgagaa ggaagaaccc tcaggaaggc ctgtacaatg aactgcagaa agataagatg   1320
gcggaggcct acagtgagat tgggatgaaa ggcgagcgcc ggaggggcaa ggggcacgat   1380
ggcctttacc agggtctcag tacagccacc aaggacacct acgacgccct tcacatgcag   1440
gccctgcccc ctcgctaa                                                 1458
```

```
<210> SEQ ID NO 47
<211> LENGTH: 485
<212> TYPE: PRT
<213> ORGANISM: Artificial Sequence
<220> FEATURE:
<223> OTHER INFORMATION: Synthesized

<400> SEQUENCE: 47

Met Ala Leu Pro Val Thr Ala Leu Leu Leu Pro Leu Ala Leu Leu Leu
1               5                   10                  15

His Ala Ala Arg Pro Glu Ile Val Met Thr Gln Ser Pro Ala Thr Leu
            20                  25                  30

Ser Val Ser Pro Gly Glu Arg Ala Thr Leu Ser Cys Arg Ala Ser Gln
        35                  40                  45

Ser Val Ser Arg Asn Leu Ala Trp Tyr Gln Gln Lys Pro Gly Gln Ala
    50                  55                  60

Pro Arg Leu Leu Ile Tyr Gly Ala Ser Thr Arg Ala Thr Gly Ile Pro
65                  70                  75                  80

Ala Arg Phe Ser Gly Ser Gly Ser Gly Thr Glu Phe Thr Leu Thr Ile
                85                  90                  95

Gly Ser Leu Gln Ser Glu Asp Phe Ala Val Tyr Tyr Cys Gln Gln Tyr
            100                 105                 110

Lys Thr Trp Pro Arg Thr Phe Gly Gln Gly Thr Asn Val Glu Ile Lys
        115                 120                 125

Gly Gly Gly Gly Ser Gly Gly Gly Ser Gly Gly Gly Ser Gln
    130                 135                 140

Val Gln Leu Gln Gln Trp Gly Ala Gly Leu Leu Lys Pro Ser Glu Thr
145                 150                 155                 160

Leu Ser Leu Thr Cys Ala Val Phe Gly Gly Ser Phe Ser Gly Tyr Tyr
                165                 170                 175

Trp Ser Trp Ile Arg Gln Pro Pro Gly Lys Gly Leu Glu Trp Ile Gly
            180                 185                 190

Glu Ile Asn His Arg Gly Asn Thr Asn Asp Asn Pro Ser Leu Lys Ser
        195                 200                 205

Arg Val Thr Ile Ser Val Asp Thr Ser Lys Asn Gln Phe Ala Leu Lys
    210                 215                 220

Leu Ser Ser Val Thr Ala Ala Asp Thr Ala Val Tyr Tyr Cys Ala Arg
225                 230                 235                 240

Glu Arg Gly Tyr Thr Tyr Gly Asn Phe Asp His Trp Gly Gln Gly Thr
                245                 250                 255

Leu Val Thr Val Ser Ser Thr Thr Thr Pro Ala Pro Arg Pro Pro Thr
            260                 265                 270

Pro Ala Pro Thr Ile Ala Ser Gln Pro Leu Ser Leu Arg Pro Glu Ala
        275                 280                 285

Cys Arg Pro Ala Ala Gly Gly Ala Val His Thr Arg Gly Leu Asp Phe
    290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
        355                 360                 365
```

```
Gly Gly Cys Glu Leu Arg Val Lys Phe Ser Arg Ser Ala Asp Ala Pro
    370             375             380

Ala Tyr Gln Gln Gly Gln Asn Gln Leu Tyr Asn Glu Leu Asn Leu Gly
385             390             395                         400

Arg Arg Glu Glu Tyr Asp Val Leu Asp Lys Arg Arg Gly Arg Asp Pro
            405             410                     415

Glu Met Gly Gly Lys Pro Arg Arg Lys Asn Pro Gln Glu Gly Leu Tyr
        420             425             430

Asn Glu Leu Gln Lys Asp Lys Met Ala Glu Ala Tyr Ser Glu Ile Gly
        435             440             445

Met Lys Gly Glu Arg Arg Arg Gly Lys Gly His Asp Gly Leu Tyr Gln
    450             455             460

Gly Leu Ser Thr Ala Thr Lys Asp Thr Tyr Asp Ala Leu His Met Gln
465             470             475                         480

Ala Leu Pro Pro Arg
            485
```

MODIFIED CELL WITH ENHANCED MIGRATION CAPABILITY

CROSS REFERENCE TO RELATED APPLICATIONS

This application claims the benefit of U.S. Provisional Application No. 62/775,168, filed Dec. 4, 2018, which are incorporated by reference herein in its entirety.

SEQUENCE LISTING INFORMATION

A computer readable textfile, entitled "Sequence Listing_ST25.txt," created on or about Nov. 12, 2019, with a file size of about 61 KB, contains the sequence listing for this application and is hereby incorporated by reference in its entirety.

TECHNICAL FIELD

The present disclosure relates to compositions and methods related to chimeric antigen receptor cells and uses thereof in the treatment of diseases, including cancer.

BACKGROUND

Cancer is known as malignant tumors involving abnormal cell growth with the potential to invade or spread to other parts of the body. In humans, there are more than one hundred types of cancer. Normally, once cancer cells are exfoliated, they spread over the entire body via the blood and/or lymph systems and therefore become life-threatening. Currently, CAR-T therapy appears not to be effective for treating solid tumor cancers. One of the challenges is that CAR-T cells seem not to be able to migrate effectively towards these cancer cells spreading over the body.

SUMMARY

Embodiments relate to a modified T cell comprising an antigen binding molecule, wherein expression and/or function of CDC42 in the modified cell has been enhanced. In embodiments, the modified cell has an increased level of cytokine release in response to an antigen that the antigen binding molecule binds as compared to a corresponding T cell that does not overexpress CDC42. In embodiments, the cytokine release comprises a cytokine release of IFNγ or GRAM B. In embodiments, the modified cell has an enhanced migration capability in response to a chemokine as compared to a corresponding T cell that does not overexpress CDC42.

This Summary is not intended to identify key features or essential features of the claimed subject matter, nor is it intended to be used to limit the scope of the claimed subject matter.

BRIEF DESCRIPTION OF THE DRAWINGS

The Detailed Description is described with reference to the accompanying figures. The use of the same reference numbers in different figures indicates similar or identical items.

DETAILED DESCRIPTION

Figure 1:
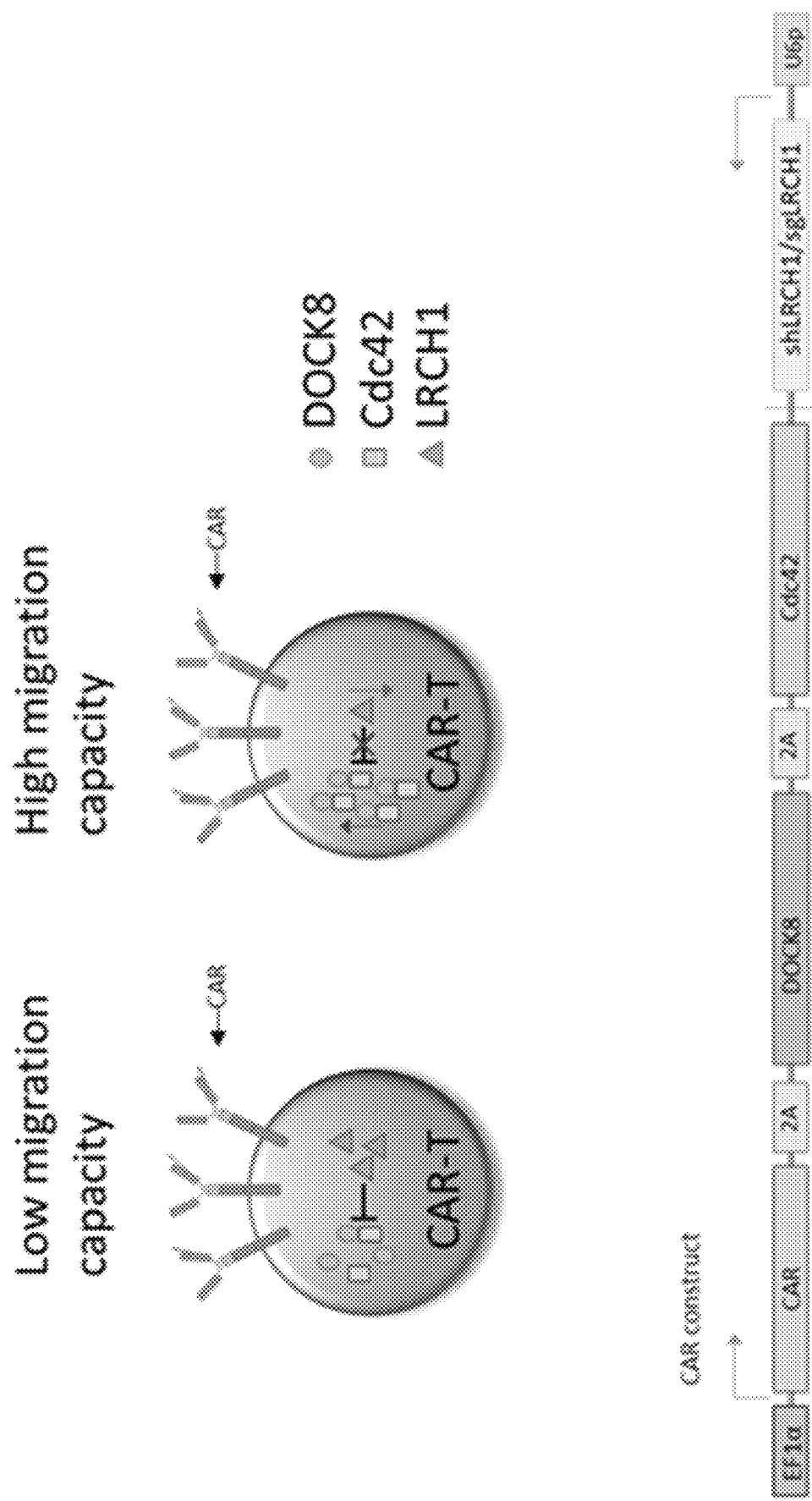
FIG. 1 shows an example of CAR construct and examples of CAR T cells.

Unless defined otherwise, all technical and scientific terms used herein have the same meaning as commonly understood by those of ordinary skill in the art to which the disclosure belongs. Although any method and material similar or equivalent to those described herein can be used in the practice or testing of the present disclosure, preferred methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 20, 15, 10, 9, 8, 7, 6, 5, 4, 3, 2 or 1% to a reference quantity, level, value, number, frequency, percentage, dimension, size, amount, weight or length.

The term "activation," as used herein, refers to the state of a cell that has been sufficiently stimulated to induce detectable cellular proliferation. Activation can also be associated with induced cytokine production and detectable effector functions. The term "activated T cells" refers to, among other things, T cells that are undergoing cell division.

The term "antibody" is used in the broadest sense and refers to monoclonal antibodies (including full length monoclonal antibodies), polyclonal antibodies, multi-specific antibodies (e.g., bispecific antibodies), and antibody fragments so long as they exhibit the desired biological activity or function. The antibodies in the present disclosure may exist in a variety of forms including, for example, polyclonal antibodies; monoclonal antibodies; Fv, Fab, Fab', and F(ab)2 and fragments; as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragments" refers to a portion of a full-length antibody, for example, the antigen binding or variable region of the antibody. Other examples of antibody fragments include Fab, Fab', F(ab')2, and Fv fragments; diabodies; linear antibodies; single-chain antibody molecules; and multi-specific antibodies formed from antibody fragments.

The term "Fv" refers to the minimum antibody fragment which contains a complete antigen-recognition and -binding site. This fragment consists of a dimer of one heavy- and one light-chain variable region domain in tight, non-covalent association. From the folding of these two domains emanates six hypervariable loops (3 loops each from the H and L chain) that contribute amino acid residues for antigen binding and confer antigen binding specificity to the antibody. However, even a single variable domain (or half of an Fv including only three complementarity determining regions (CDRs) specific for an antigen) has the ability to recognize and bind antigen, although at a lower affinity than the entire binding site (the dimer).

An "antibody heavy chain," as used herein, refers to the larger of the two types of polypeptide chains present in all antibody molecules in their naturally occurring conformations. An "antibody light chain," as used herein, refers to the smaller of the two types of polypeptide chains present in all antibody molecules in their naturally occurring conformations. K and λ light chains refer to the two major antibody light chain isotypes.

The term "synthetic antibody" refers to an antibody which is generated using recombinant DNA technology, such as, for example, an antibody expressed by a bacteriophage. The term also includes an antibody which has been generated by the synthesis of a DNA molecule encoding the antibody and the expression of the DNA molecule to obtain the antibody or to obtain an amino acid encoding the antibody. The synthetic DNA is obtained using technology that is available and well known in the art.

The term "antigen" refers to a molecule that provokes an immune response, which may involve either antibody production, or the activation of specific immunologically-competent cells, or both. Antigens include any macromolecule, including all proteins or peptides, or molecules derived from recombinant or genomic DNA. For example, DNA including a nucleotide sequence or a partial nucleotide sequence encoding a protein or peptide that elicits an immune response, and therefore, encodes an "antigen" as the term is used herein. An antigen need not be encoded solely by a full-length nucleotide sequence of a gene. An antigen can be generated, synthesized or derived from a biological sample including a tissue sample, a tumor sample, a cell, or a biological fluid.

The term "anti-tumor effect" as used herein, refers to a biological effect associated with a decrease in tumor volume, a decrease in the number of tumor cells, a decrease in the number of metastases, decrease in tumor cell proliferation, decrease in tumor cell survival, an increase in life expectancy of a subject having tumor cells, or amelioration of various physiological symptoms associated with the cancerous condition. An "anti-tumor effect" can also be manifested by the ability of the peptides, polynucleotides, cells, and antibodies in the prevention of the occurrence of tumors in the first place.

The term "auto-antigen" refers to an endogenous antigen mistakenly recognized by the immune system as being foreign. Auto-antigens include cellular proteins, phosphoproteins, cellular surface proteins, cellular lipids, nucleic acids, glycoproteins, including cell surface receptors.

The term "autologous" is used to describe a material derived from a subject that is subsequently re-introduced into the same subject.

The term "allogeneic" is used to describe a graft derived from a different subject of the same species. As an example, a donor subject may be a related or unrelated or recipient subject, but the donor subject has immune system markers that are similar to the recipient subject.

The term "xenogeneic" is used to describe a graft derived from a subject of a different species. As an example, the donor subject is from a different species than a recipient subject, and the donor subject and the recipient subject can be genetically and immunologically incompatible.

The term "cancer" is used to refer to a disease characterized by the rapid and uncontrolled growth of aberrant cells. Cancer cells can spread locally or through the bloodstream and lymphatic system to other parts of the body. Examples of various cancers include breast cancer, prostate cancer, ovarian cancer, cervical cancer, skin cancer, pancreatic cancer, colorectal cancer, renal cancer, liver cancer, brain cancer, lymphoma, leukemia, lung cancer, and the like.

Throughout this specification, unless the context requires otherwise, the words "comprise," "includes" and "including" will be understood to imply the inclusion of a stated step or element or group of steps or elements but not the exclusion of any other step or element or group of steps or elements.

The phrase "consisting of" is meant to include, and is limited to, whatever follows the phrase "consisting of." Thus, the phrase "consisting of" indicates that the listed elements are required or mandatory and that no other elements may be present.

The phrase "consisting essentially of" is meant to include any element listed after the phrase and can include other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base-pairing rules, or there may be "complete" or "total" complementarity between the nucleic acids. The degree of complementarity between nucleic acid strands has significant effects on the efficiency and strength of hybridization between nucleic acid strands.

The term "corresponds to" or "corresponding to" refers to (a) a polynucleotide having a nucleotide sequence that is substantially identical or complementary to all or a portion of a reference polynucleotide sequence or encoding an amino acid sequence identical to an amino acid sequence in a peptide or protein; or (b) a peptide or polypeptide having an amino acid sequence that is substantially identical to a sequence of amino acids in a reference peptide or protein.

The term "co-stimulatory ligand," refers to a molecule on an antigen-presenting cell (e.g., an APC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including at least one of proliferation, activation, differentiation, and other cellular responses. A co-stimulatory ligand can include B7-1 (CD80), B7-2 (CD86), PD-L1, PD-L2, 4-1BBL, OX40L, inducible co-stimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, a ligand for CD7, an agonist or antibody that binds the Toll ligand receptor and a ligand that specifically binds with B7-H3. A co-stimulatory ligand also includes, inter alia, an agonist or an antibody that specifically binds with a co-stimulatory molecule present on a T cell, such as CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds CD83.

The term "co-stimulatory molecule" refers to the cognate binding partner on a T cell that specifically binds with a co-stimulatory ligand, thereby mediating a co-stimulatory response by the T cell, such as proliferation. Co-stimulatory molecules include an MHC class I molecule, BTLA, and a Toll-like receptor.

The term "co-stimulatory signal" refers to a signal, which in combination with a primary signal, such as TCR/CD3 ligation, leads to T cell proliferation and/or upregulation or downregulation of key molecules. The terms "disease" and "condition" may be used interchangeably or may be different in that the particular malady or condition may not have a known causative agent (so that etiology has not yet been worked out), and it is therefore not yet recognized as a disease but only as an undesirable condition or syndrome, wherein a more or less specific set of symptoms have been identified by clinicians. The term "disease" is a state of health of a subject wherein the subject cannot maintain homeostasis, and wherein if the disease is not ameliorated, then the subject's health continues to deteriorate. In contrast, a "disorder" in a subject is a state of health in which the animal is able to maintain homeostasis, but in which the animal's state of health is less favorable than it would be in the absence of the disorder. Left untreated, a disorder does not necessarily cause a further decrease in the animal's state of health.

The term "effective" refers to adequate to accomplish a desired, expected, or intended result. For example, an "effective amount" in the context of treatment may be an amount of a compound sufficient to produce a therapeutic or prophylactic benefit.

The term "encoding" refers to the inherent property of specific sequences of nucleotides in a polynucleotide, such as a gene, a cDNA, or an mRNA, to serve as a template for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence (except that a "T" is replaced by a "U") and is usually provided in sequence listings, and the non-coding strand, used as the template for transcription of a gene or cDNA, can be referred to as encoding the protein or other product of that gene or cDNA.

The term "exogenous" refers to a molecule that does not naturally occur in a wild-type cell or organism but is typically introduced into the cell by molecular biological techniques. Examples of exogenous polynucleotides include vectors, plasmids, and/or man-made nucleic acid constructs encoding the desired protein. With regard to polynucleotides and proteins, the term "endogenous" or "native" refers to naturally-occurring polynucleotide or amino acid sequences that may be found in a given wild-type cell or organism. Also, a particular polynucleotide sequence that is isolated from a first organism and transferred to a second organism by molecular biological techniques is typically considered an "exogenous" polynucleotide or amino acid sequence with respect to the second organism. In specific embodiments, polynucleotide sequences can be "introduced" by molecular biological techniques into a microorganism that already contains such a polynucleotide sequence, for instance, to create one or more additional copies of an otherwise naturally-occurring polynucleotide sequence, and thereby facilitate overexpression of the encoded polypeptide.

The term "expression or overexpression" refers to the transcription and/or translation of a particular nucleotide sequence into a precursor or mature protein, for example, driven by its promoter. "Overexpression" refers to the production of a gene product in transgenic organisms or cells that exceeds levels of production in normal or non-transformed organisms or cells. As defined herein, the term "expression" refers to expression or overexpression.

The term "expression vector" refers to a vector including a recombinant polynucleotide including expression control (regulatory) sequences operably linked to a nucleotide sequence to be expressed. An expression vector includes sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

The term "homologous" refers to sequence similarity or sequence identity between two polypeptides or between two polynucleotides when a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared× 100. For example, if 6 of 10 of the positions in two sequences are matched or homologous, then the two sequences are 60% homologous. By way of example, the DNA sequences ATTGCC and TATGGC share 50% homology. A comparison is made when two sequences are aligned to give maximum homology.

The term "immunoglobulin" or "Ig," refers to a class of proteins, which function as antibodies. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function but may serve as an antigen receptor. IgE is the immunoglobulin that mediates immediate hypersensitivity by causing the release of mediators from mast cells and basophils upon exposure to the allergen.

The term "isolated" refers to a material that is substantially or essentially free from components that normally accompany it in its native state. The material can be a cell or a macromolecule such as a protein or nucleic acid. For example, an "isolated polynucleotide," as used herein, refers to a polynucleotide, which has been purified from the sequences which flank it in a naturally-occurring state, e.g., a DNA fragment which has been removed from the sequences that are normally adjacent to the fragment. Alternatively, an "isolated peptide" or an "isolated polypeptide" and the like, as used herein, refer to in vitro isolation and/or purification of a peptide or polypeptide molecule from its natural cellular environment, and from association with other components of the cell.

The term "substantially purified" refers to a material that is substantially free from components that are normally associated with it in its native state. For example, a substantially purified cell refers to a cell that has been separated from other cell types with which it is normally associated in its naturally occurring or native state. In some instances, a population of substantially purified cells refers to a homogenous population of cells. In other instances, this term refers simply to a cell that has been separated from the cells with which they are naturally associated in their natural state. In embodiments, the cells are cultured in vitro. In embodiments, the cells are not cultured in vitro.

In the context of the present disclosure, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. Moreover, the use of lentiviruses enables the integration of the genetic information into the host chromosome, resulting in stably transduced genetic information. HIV, SIV, and FIV are all examples of lentiviruses. Vectors derived from lentiviruses offer the means to achieve significant levels of gene transfer in vivo.

The term "modulating," refers to mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response, thereby mediating a beneficial therapeutic response in a subject, preferably, a human.

Nucleic acid is "operably linked" when it is placed into a functional relationship with another polynucleotide. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation.

The term "under transcriptional control" refers to a promoter being operably linked to and in the correct location and orientation in relation to a polynucleotide to control (regulate) the initiation of transcription by RNA polymerase and expression of the polynucleotide.

The term "overexpressed" tumor antigen or "overexpression" of the tumor antigen is intended to indicate an abnormal level of expression of the tumor antigen in a cell from a disease area such as a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

Cancers that may be treated include tumors that are not vascularized, or not yet substantially vascularized, as well as vascularized tumors. The cancers may include non-solid tumors (such as hematological tumors, for example, leukemia, lymphoma, and multiple myeloma) or may include solid tumors. Types of cancers to be treated with the CARs of the disclosure include, but are not limited to, carcinoma, blastoma, and sarcoma, and certain leukemia or lymphoid malignancies, benign and malignant tumors, and malignancies, e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme), astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma, and brain metastases).

A solid tumor antigen is an antigen expressed on a solid tumor. In embodiments, the solid tumor antigen is also expressed at low levels on healthy tissue. Examples of solid tumor antigens and their related disease tumors are provided in Table 1A.

TABLE 1A

| Solid Tumor antigen | Disease tumor |
|---|---|
| PRLR | Breast Cancer |
| CLCA1 | colorectal cancer |
| MUC12 | colorectal cancer |
| GUCY2C | colorectal cancer |
| GPR35 | colorectal cancer |
| CR1L | Gastric Cancer |
| MUC 17 | Gastric Cancer |
| TMPRSS11B | esophageal cancer |
| MUC21 | esophageal cancer |
| TMPRSS11E | esophageal cancer |
| CD207 | bladder Cancer |
| SLC30A8 | pancreatic Cancer |
| CFC1 | pancreatic Cancer |
| SLC12A3 | Cervical Cancer |
| SSTR1 | Cervical tumor |
| GPR27 | Ovary tumor |
| FZD10 | Ovary tumor |
| TSHR | Thyroid Tumor |
| SIGLEC15 | Urothelial cancer |
| SLC6A3 | Renal cancer |
| KISS1R | Renal cancer |
| QRFPR | Renal cancer: |
| GPR119 | Pancreatic cancer |
| CLDN6 | Endometrial cancer/Urothelial cancer |
| UPK2 | Urothelial cancer (including bladder cancer) |
| ADAM12 | Breast cancer, pancreatic cancer and the like |
| SLC45A3 | Prostate cancer |
| ACPP | Prostate cancer |
| MUC21 | Esophageal cancer |
| MUC16 | Ovarian cancer |
| MS4A12 | Colorectal cancer |
| ALPP | Endometrial cancer |
| CEA | Colorectal carcinoma |
| EphA2 | Glioma |
| FAP | Mesothelioma |
| GPC3 | Lung squamous cell carcinoma |
| IL13-Rα2 | Glioma |
| Mesothelin | Metastatic cancer |
| PSMA | Prostate cancer |
| ROR1 | Breast lung carcinoma |
| VEGFR-II | Metastatic cancer |
| GD2 | Neuroblastoma |
| FR-α | Ovarian carcinoma |
| ErbB2 | Carcinomas |
| EpCAM | Carcinomas |
| EGFRvIII | Glioma-Glioblastoma |
| EGFR | Glioma-NSCL cancer |
| tMUC 1 | Cholangiocarcinoma, Pancreatic cancer, Breast Cancer |
| B7-H3 | Ewing sarcoma (bone tumor), rhabdomyosarcoma, nephroblastoma, neuroblastoma and medulloblastoma (brain tumor) |

The term "parenteral administration" of a composition includes, e.g., subcutaneous (s.c.), intravenous (i.v.), intramuscular (i.m.), intrasternal injection, or infusion techniques.

The terms "patient," "subject," and "individual," and the like are used interchangeably herein and refer to any human, or animal, amenable to the methods described herein. In certain non-limiting embodiments, the patient, subject, or individual is a human or animal. In embodiments, the term "subject" is intended to include living organisms in which an immune response can be elicited (e.g., mammals). Examples of subjects include humans, and animals such as dogs, cats, mice, rats, and transgenic species thereof.

A subject in need of treatment or in need thereof includes a subject having a disease, condition, or disorder that needs to be treated. A subject in need thereof also includes a subject that needs treatment for the prevention of a disease, condition, or disorder. In embodiments, the disease, condition, or disorder is cancer.

The term "polynucleotide" or "nucleic acid" refers to mRNA, RNA, cRNA, rRNA, cDNA or DNA. The term typically refers to a polymeric form of nucleotides of at least 10 bases in length, either ribonucleotides or deoxynucleotides or a modified form of either type of nucleotide. The term includes all forms of nucleic acids including single and double-stranded forms of nucleic acids.

The terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted or replaced with different nucleotides. In this regard, it is well understood in the art that certain alterations inclusive of mutations, additions, deletions, and substitutions can be made to a reference polynucleotide whereby the altered polynucleotide retains the biological function or activity of the reference polynucleotide or has increased activity in relation to the reference polynucleotide (i.e., optimized). Polynucleotide variants include, for example, polynucleotides having at least 50% (and at least 51% to at least 99% and all integer percentages in between, e.g., 90%, 95%, or 98%) sequence identity with a reference polynucleotide sequence described herein. The terms "polynucleotide variant" and "variant" also include naturally-occurring allelic variants and orthologs.

The terms "polypeptide," "polypeptide fragment," "peptide," and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. In certain aspects, polypeptides may include enzymatic polypeptides, or "enzymes," which typically catalyze (i.e., increase the rate of) various chemical reactions.

The term "polypeptide variant" refers to polypeptides that are distinguished from a reference polypeptide sequence by the addition, deletion, or substitution of at least one amino acid residue. In certain embodiments, a polypeptide variant is distinguished from a reference polypeptide by one or more substitutions, which may be conservative or non-conservative. In certain embodiments, the polypeptide variant comprises conservative substitutions and, in this regard, it is well understood in the art that some amino acids may be changed to others with broadly similar properties without changing the nature of the activity of the polypeptide. Polypeptide variants also encompass polypeptides in which one or more amino acids have been added or deleted or replaced with different amino acid residues.

The term "promoter" refers to a DNA sequence recognized by the synthetic machinery of the cell or introduced synthetic machinery, required to initiate the specific transcription of a polynucleotide sequence. The term "expression control (regulatory) sequences" refers to DNA sequences necessary for the expression of an operably linked coding sequence in a particular host organism. The control (regulatory) sequences that are suitable for prokaryotes, for example, include a promoter, optionally an operator sequence, and a ribosome binding site. Eukaryotic cells are known to utilize promoters, polyadenylation signals, and enhancers.

The term "bind," "binds," or "interacts with" refers to a molecule recognizing and adhering to a second molecule in a sample or organism but does not substantially recognize or adhere to other structurally unrelated molecules in the sample. The term "specifically binds," as used herein with respect to an antibody, refers to an antibody which recognizes a specific antigen, but does not substantially recognize or bind other molecules in a sample. For example, an antibody that specifically binds an antigen from one species may also bind that antigen from one or more species. But, such cross-species reactivity does not itself alter the classification of an antibody as specific. In another example, an antibody that specifically binds an antigen may also bind different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds a specific protein structure rather than to any protein. If an antibody is specific for epitope "A," the presence of a molecule containing epitope A (or free, unlabeled A), in a reaction containing labeled "A" and the antibody, will reduce the amount of labeled A bound to the antibody.

By "statistically significant," it is meant that the result was unlikely to have occurred by chance. Statistical significance can be determined by any method known in the art. Commonly used measures of significance include the p-value, which is the frequency or probability with which the observed event would occur if the null hypothesis were true. If the obtained p-value is smaller than the significance level, then the null hypothesis is rejected. In simple cases, the significance level is defined at a p-value of 0.5 or less. A "decreased" or "reduced" or "lesser" amount is typically a "statistically significant" or a physiologically significant amount, and may include a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein.

The term "stimulation," refers to a primary response induced by binding of a stimulatory molecule (e.g., a TCR/CD3 complex) with its cognate ligand thereby mediating a signal transduction event, such as signal transduction via the TCR/CD3 complex. Stimulation can mediate altered expression of certain molecules, such as downregulation of TGF-β, and/or reorganization of cytoskeletal structures.

The term "stimulatory molecule" refers to a molecule on a T cell that specifically binds a cognate stimulatory ligand present on an antigen-presenting cell. For example, a functional signaling domain derived from a stimulatory molecule is the zeta chain associated with the T cell receptor complex. The stimulatory molecule includes a domain responsible for signal transduction.

The term "stimulatory ligand" refers to a ligand that when present on an antigen-presenting cell (e.g., an APC, a dendritic cell, a B-cell, and the like.) can specifically bind with a cognate binding partner (referred to herein as a "stimulatory molecule") on a cell, for example a T cell, thereby mediating a primary response by the T cell, including activation, initiation of an immune response, proliferation, and similar processes. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "therapeutic" refers to treatment and/or prophylaxis. A therapeutic effect is obtained by suppression, remission, or eradication of a disease state or alleviating the symptoms of a disease state.

The term "therapeutically effective amount" refers to the amount of the subject compound that will elicit the biological or medical response of a tissue, system, or subject that is being sought by the researcher, veterinarian, medical doctor or another clinician. The term "therapeutically effective amount" includes that amount of a compound that, when administered, is sufficient to prevent the development of, or alleviate to some extent, one or more of the signs or symptoms of the disorder or disease being treated. The therapeutically effective amount will vary depending on the compound, the disease and its severity and the age, weight, and other factors, of the subject to be treated.

The term "treat a disease" refers to the reduction of the frequency or severity of at least one sign or symptom of a disease or disorder experienced by a subject.

The term "transfected" or "transformed" or "transduced" refers to a process by which an exogenous nucleic acid is transferred or introduced into the host cell. A "transfected" or "transformed" or "transduced" cell is one which has been transfected, transformed, or transduced with exogenous nucleic acid. The cell includes the primary subject cell and its progeny.

The term "vector" refers to a polynucleotide that comprises an isolated nucleic acid and which can be used to deliver the isolated nucleic acid to the interior of a cell. Numerous vectors are known in the art including linear polynucleotides, polynucleotides associated with ionic or amphiphilic compounds, plasmids, and viruses. Thus, the term "vector" includes an autonomously replicating plasmid or a virus. The term also includes non-plasmid and non-viral compounds which facilitate the transfer of nucleic acid into cells, such as, for example, polylysine compounds, liposomes, and the like. Examples of viral vectors include adenoviral vectors, adeno-associated virus vectors, retroviral vectors, and others. For example, lentiviruses are complex retroviruses, which, in addition to the common retroviral genes gag, pol, and env, contain other genes with regulatory or structural function. Lentiviral vectors are well known in the art. Some examples of lentivirus include the Human Immunodeficiency Viruses: HIV-1, HIV-2, and the Simian Immunodeficiency Virus: SIV. Lentiviral vectors have been generated by multiply attenuating the HIV virulence genes, for example, the genes env, vif, vpr, vpu, and nef are deleted making the vector biologically safe.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

A "chimeric antigen receptor" (CAR) molecule is a recombinant polypeptide including at least an extracellular domain, a transmembrane domain, and a cytoplasmic domain or intracellular domain. In embodiments, the domains of the CAR are on the same polypeptide chain, for example, a chimeric fusion protein. In embodiments, the domains are on different polypeptide chains, for example, the domains are not contiguous.

The extracellular domain of a CAR molecule includes an antigen binding domain. In embodiments, the antigen binding domain binds an antigen, for example, a cell surface molecule or marker, on the surface of a B cell. In embodiments, the cell surface molecule of a B cell includes CD19, CD22, CD20, BCMA, CD5, CD7, CD2, CD16, CD56, CD30, CD14, CD68, CD11b, CD18, CD169, CD1c, CD33, CD38, CD138, or CD13. In embodiments, the cell surface molecule of the B cell is CD19, CD20, CD22, or BCMA. In embodiments, the cell surface molecule of the B cell is CD19.

In embodiments, the antigen binding domain binds an antigen on the surface of a tumor, for example, a tumor antigen or tumor marker. Tumor antigens are proteins that are produced by tumor cells that elicit an immune response, particularly T cell-mediated immune response. Tumor antigens are well known in the art and include, for example, tumor-associated MUC1 (tMUC1), a glioma-associated antigen, carcinoembryonic antigen (CEA), 8-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, Survivin, telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin. For example, when the tumor antigen is CD19, and the CAR thereof can be referred to as CD19CAR, and the T cell comprising CD19CAR can be referred to a CART19 cell or CD19CAR T cell.

In embodiments, the extracellular antigen binding domain of a CAR includes at least one scFv or at least a single domain antibody. As an example, there can be two scFvs on a CAR. The scFv includes a light chain variable (VL) region and a heavy chain variable (VH) region of a target antigen-specific monoclonal antibody joined by a flexible linker. Single chain variable region fragments can be made by linking light and/or heavy chain variable regions by using a short linking peptide (Bird et al., Science 242:423-426, 1988). An example of a linking peptide is the GS linker having the amino acid sequence (GGGGS)3 (SEQ ID NO: 2), which bridges approximately 3.5 nm between the carboxy terminus of one variable region and the amino terminus of the other variable region. Linkers of other sequences have been designed and used (Bird et al., 1988, supra). In general, linkers can be short, flexible polypeptides comprising about 20 or fewer amino acid residues. The single-chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as E. coli. Polynucleotides encoding the scFv of interest can be made by routine manipulations such as ligation of polynucleotides. The resultant scFv can be isolated using standard protein purification techniques known in the art.

In embodiments, the CAR molecules described herein comprises one or more CDRs for binding an antigen of interest, for example, one or more CDRs for binding CD19 or tMUC1.

The cytoplasmic domain of the CAR molecules described herein includes one or more co-stimulatory domains and one or more signaling domains. The co-stimulatory and signaling domains function to transmit the signal and activate molecules, such as T cells, in response to antigen binding. The one or more co-stimulatory domains are derived from stimulatory molecules and/or co-stimulatory molecules, and the signaling domain is derived from a primary signaling domain, such as the CD3 zeta domain. In embodiments, the signaling domain further includes one or more functional signaling domains derived from a co-stimulatory molecule. In embodiments, the co-stimulatory molecules are cell surface molecules (other than antigens receptors or their ligands) that are required for activating a cellular response to an antigen.

In embodiments, the co-stimulatory domain includes the intracellular domain of CD27, CD28, 4-1BB, OX40, CD30, CD40, PD-1, ICOS, lymphocyte function-associated antigen-1 (LFA-1), CD2, CD7, LIGHT, NKG2C, B7-H3, a ligand that specifically binds CD83, or any combination thereof. In embodiments, the signaling domain includes a CD3 zeta domain derived from a T cell receptor.

In embodiments, the cytoplasmic domain of the CAR only includes one or more stimulatory domains and no signaling domain.

The CAR molecules also include a transmembrane domain. The incorporation of a transmembrane domain in the CAR molecules stabilizes the molecule. In embodiments, the transmembrane domain of the CAR molecules is the transmembrane domain of a CD28 or 4-1BB molecule.

Between the extracellular domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain on the polypeptide chain. A spacer domain may include up to 300 amino acids, preferably 10 to 100 amino acids, and most preferably 25 to 50 amino acids.

CAR Molecule(s) and Therapeutic Agent(s)

The present disclosure describes a cell modified to express one or more molecules at a level that is higher or lower than the level of the one or more molecules expressed by a cell that has not been modified to express the one or more molecules, wherein the one or more molecules are associated with cell migration. Embodiments also describe a modified cell engineered to express an antigen binding molecule, wherein expression and/or function of one or more molecules in the modified cell has been enhanced or reduced, wherein the one or more molecules are associated with cell migration. In embodiments, the modified cell comprises a disruption in an endogenous gene or an addition of exogenous gene that is associated with a biosynthesis or transportation pathway of the one or more molecules. As used herein, the term "associated with cell migration" refers to being involved with cell migration. As an example, "a molecule associated with cell migration" means that the molecule can activate, induce, disrupt, or inhibit cell migration.

The terms "trafficking ability" and "migration ability" of cells and the like are used interchangeably herein and refer to the ability or capability of cells (e.g., T cells) migration in response to, for example, chemokines and stimulation (e.g., tumor environment). Examples of the chemokines may include CCL1, CCL5, CCL2, CCL22, CCL17, CXCL9, and CXCL10, CXCL11. For example, modified T cells overexpressing CDC42 or having reduced expression of LRCH1 show enhanced migration ability in the migration assay. As shown in the Example below, the number of the modified cells migrate or traffic to the medium containing CCL5 is greater than that of T cells neither overexpressing CDC42 nor having reduced expression of LRCH1.

Embodiments described herein relate to a method or use of polynucleotide, the method comprising providing a viral particle (e.g., AAV, lentivirus or their variants) comprising a vector genome, the vector genome comprising the polynucleotide encoding the one more molecules and a polynucleotide encoding a binding molecule, the polynucleotide operably linked to an expression control element conferring transcription of the polynucleotides; and administering an amount of the viral particle to a subject such that the polynucleotide is expressed in the subject, where the one or more molecules are associated with cell migration. In embodiments, the AAV preparation may include AAV vector particles, empty capsids and host cell impurities, thereby providing an AAV product substantially free of AAV empty capsids.

Embodiments described herein relate to a pharmaceutical composition comprising the population of the modified cells described herein. Embodiments also describe a method of causing or eliciting T cell response in a subject in need thereof and/or treating a tumor of the subject, the method comprising administering an effective amount of the pharmaceutical composition to the subject. Embodiments described herein also relate to an isolated nucleic acid sequence encoding one or more molecules that are associated with cell migration.

In embodiments, the one or more molecules comprise at least one of DOCK8, CDC42, and LRCH1, a functional variant of the one or more molecules, or a functional fragment of the one or more molecules. In embodiments, the one or more molecules are or comprise CDC42, which is overexpressed in the modified T cells. In embodiments, the one or more molecules are or comprise LRCH1 of which expression is reduced in the modified T cells. In embodiments, the modified cell comprises a recombinant polynucleotide encoding SEQ ID NOS: 43 and/or 39. In embodiments, the modified cell comprises a recombinant polynucleotide comprising SEQ ID NO: 38. In embodiments, the modified cell comprises a recombinant polynucleotide encoding SEQ ID NOS: 43 and encoding an antigen binding molecule (e.g., CAR). In embodiments, the modified cell comprises a recombinant polynucleotide comprising SEQ ID NO: 38 and encoding an antigen binding molecule (e.g., CAR). In embodiments, the modified cell comprises at least one of SEQ ID Nos: 44-47.

Cell division control protein 42 homolog, also known as Cdc42, is a protein involved in regulation of the cell cycle. It was originally identified in *S. cerevisiae* (yeast) as a mediator of cell division and is now known to influence a variety of signaling events and cellular processes in a variety of organisms from yeast to mammals. DOCK8 (Dedicator of cytokinesis 8), also known as Zir3, is a large (~190 kDa) protein involved in intracellular signaling networks and is a member of the DOCK-C subfamily of the DOCK family of guanine nucleotide exchange factors (GEFs) which function as activators of small G proteins. Leucine-rich repeat and calponin homology domain-containing protein 1 (LRCH1) includes a leucine-rich repeat and a calponin homology domain, and function as a negative regulator of GTPase CDC42 by sequestering CDC42-guanine exchange factor DOCK8, probably by preventing CDC42 activation and negatively regulates CD4+ T-cell migration.

In embodiments, the polynucleotide may integrate into the genome of the modified cell, and descendants of the modified cell will also express the polynucleotide, resulting in a stably transfected modified cell. In embodiments, the modified cell may express the polynucleotide encoding the CAR but the polynucleotide does not integrate into the genome of the modified cell such that the modified cell expresses the transiently transfected polynucleotide for a finite period of time, for example a few days, after which the polynucleotide is lost through cell division or other cellular processes. As an example, the polynucleotide is present in the modified cell in a recombinant DNA construct, in an mRNA, or in a viral vector, and/or the polynucleotide is an mRNA, which is not integrated into the genome of the modified cell.

Embodiments relate to a method or use of the polynucleotides described herein. The method or use includes: providing a viral particle (e.g., AAV, lentivirus or their variants) comprising a vector genome, the vector genome comprising the polynucleotide, wherein the polynucleotide is operably linked to an expression control element conferring transcription of the polynucleotide; and administering an amount of the viral particle to the subject such that the polynucleotide is expressed in the subject. In embodiments, the AAV preparation includes AAV vector particles, empty capsids, and host cell impurities, thereby providing an AAV product substantially free of AAV empty capsids. More information of the administration and preparation of the viral particle may be found at the U.S. Pat. No. 9,840,719 and Milani et al., Sci. Transl. Med. 11, eaav7325 (2019) 22 May 2019, which are incorporated herein by reference.

In embodiments, a bioreactor can be inoculated at a cell density of approximately $0.5 \times 10^6$ cells/mL with viability greater than 95%. When the cell density reaches approximately $1.0 \times 10^6$ cells/mL, the cells may be transfected with the polyethyleneimine (PEI)/DNA complexes (polyplexes) with a PEI to DNA ratio of 2:1. At the time of harvest, AAV from the cell culture in the bioreactor may be released using the Triton X-100 method. All solutions may be added directly to the bioreactor, and the lysate centrifuged at 4000×g for 20 min. The supernatant can be stored at −80° C. for further processing. AAV may be further purified. For example, AAV samples (12.3 mL) may be purified by overlaying them on top of a series of step gradients using 15, 25, 40, and 54% iodixanol concentrations containing 1, 5, 7, and 5 mL, respectively. The 15% iodixanol concentration also contains 1 M NaCl to avoid aggregation of AAV with other cellular proteins and negatively charged nuclear components. After the completion of centrifugation, 5 mL may be withdrawn from 2 mm below the 40/54 interface marked before starting the ultracentrifugation at 385,000×g for 1 h 45 min in Sorvals T-865 rotor in Sorval Ultracentrifuge. The viral vectors can then be quantified. For example, vectors AAV infectivity can be determined by the gene transfer assay (GTA) using GFP as a reporter gene in all cases. AAV infectivity assay, in which samples are diluted before addition to the cells, have the GFP positive cells in the range of 2-20% to ensure that only a single virus has entered the cell for GFP expression. The GFP-positive cells may be quantified by FACS using HEK293 cells in suspension. The AAV may be then administrated to a subject. For example, AAV may be diluted in 0.9% sterile NaCl saline solution (supplemented with 0.25% human serum albumin [HSA]) for infusion in patients, and the final volume of infusion can be calculated based on the patient's weight as 3 mL/kg.

In embodiments, the modified cell comprises the antigen binding molecule, and the antigen binding molecule is a CAR, which comprises an antigen-binding domain, a transmembrane domain, and an intracellular signaling domain. In embodiments, the antigen-binding domain binds a tumor antigen selected from the group consisting of: TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGSS, HMWMAA, o-acetyl-GD2, Folate receptor beta, TEM1/CD248, TEM7R, CLDN6, GPRCSD, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1. In embodiments, the intracellular signaling domain comprises a co-stimulatory signaling domain, or a primary signaling domain and a co-stimulatory signaling domain, wherein the co-stimulatory signaling domain comprises a functional signaling domain of a protein selected from the group consisting of CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11 b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D In embodiments, the modified cell comprises the antigen binding molecule, the antigen binding molecule is a modified TCR. In embodiments, the TCR is derived from spontaneously occurring tumor-specific T cells in patients. In embodiments, the TCR binds to a tumor antigen. In embodiments, the tumor antigen comprises CEA, gp100, MART-1, p53, MAGE-A3, or NY-ESO-1. In embodiments, the TCR comprises TCRγ and TCRδ Chains or TCRα and TCRβ chains, or a combination thereof.

In embodiments, the cell is an immune effector cell. (e.g., a population of immune effector cells). In embodiments, the immune effector cell is a T cell or an NK cell. In embodiments, the immune effector cell is a T cell. In embodiments, the T cell is a CD4+ T cell, a CD8+ T cell, or a combination thereof. In embodiments, the cell is a human cell.

In embodiments, the enhanced expression and/or function of the one or more molecules are implemented by introducing a nucleic acid sequence encoding the one or more molecules and/or the binding molecule, which is present in the modified cell in a recombinant DNA construct, in an mRNA, or in a viral vector. In embodiments, the nucleic acid sequence is an mRNA, which is not integrated into the genome of the modified cell. In embodiments, the nucleic acid sequence is associated with an oxygen-sensitive polypeptide domain. In embodiments, the oxygen-sensitive polypeptide domain comprises HIF VHL binding domain. In embodiments, the nucleic acid sequence is regulated by a promoter comprising a binding site for a transcription modulator that modulates the expression of the CDC42 in the cell. In embodiments, the transcription modulator is or includes Hif1a, NFAT, FOXP3, and/or NFkB.

In embodiments, expression of one or more therapeutic agents may be regulated by an inducible expression system. Examples of therapeutic agents includes cytokines. The inducible expression system allows for a temporal and spatial controlled activation and/or expression of genes. For example, Tetracycline-Controlled Transcriptional Activation is a method of inducible gene expression where transcription is reversibly turned on or off in the presence of the antibiotic tetracycline or one of its derivatives (e.g., doxycycline). For example, an inducible suicide gene expression system allows for a temporal and spatial controlled activation and/or expression of a suicide gene, which causes a cell to kill itself through apoptosis.

In embodiments, the modified cells comprise a nucleic acid sequence encoding a reverse tetracycline transactivator (rtTA). In embodiments, expression of one or more therapeutic agents is regulated by the rtTA, such that the one or more therapeutic agents are expressed in the presence of tetracycline. In embodiments, a concentration of tetracycline in the cell culture medium is not less than about 2 pg/ml. In embodiments, the tetracycline is selected from the group consisting of tetracycline, demeclocycline, meclocycline, doxycycline, lymecycline, methacycline, minocycline, oxytetracycline, rolitetracycline, and chlortetracycline. In embodiments, the tetracycline is doxycycline.

In embodiments, the inducible suicide system is an HSV-TK system or an inducible caspase-9 system. In embodiments, the modified cells comprise a nucleic acid sequence encoding a suicide gene, such that when the modified cells are in the presence of a nucleoside analogue in a manner permitting expression of the suicide gene, to render the nucleoside analogue cytotoxic to the modified cells. In embodiments, the suicide gene is selected from the group consisting of thymidine kinase of herpes simplex virus, thymidine kinase of varicella zoster virus, and bacterial cytosine deaminase. In embodiments, the suicide gene is thymidine kinase of herpes simplex virus. In embodiments, the nucleoside analogue is selected from the group consisting of ganciclovir, acyclovir, buciclovir, famciclovir, penciclovir, valciclovir, trifluorothymidine, 1-[2-deoxy, 2-fluoro, beta-D-arabino furanosyl]-5-iodouracil, ara-A, araT 1-beta-D-arabinofuranoxyl thymine, 5-ethyl-2'-deoxyuridine, 5-iodo-5'-amino-2,5'-dideoxyuridine, idoxuridine, AZT, AIU, dideoxycytidine, and AraC. In embodiments, the nucleoside analogue is ganciclovir.

Embodiments relate to a modified T cell comprising an antigen binding molecule, wherein expression and/or function of CDC42 in the modified cell has been enhanced. In embodiments, the modified cell has an enhanced T cell response. For example, the T cell response may be measured based on a level of cytokine releases, a level of protease releases, and/or migration capability. In embodiments, the modified cell has an increased level of cytokine release in response to an antigen that the antigen binding molecule binds as compared to a corresponding T cell that does not overexpress CDC42. In embodiments, the cytokine release comprises a cytokine release of IFNγ. In embodiments, the protease release comprises a protease release of Granzyme B (GRAM B). Granzyme B is a serine protease most commonly found in the granules of natural killer cells (NK cells) and cytotoxic T cells. It is secreted by these cells along with the pore forming protein perforin to mediate apoptosis in target cells. Granzyme B has also more recently found to be produced by a wide range of non-cytotoxic cells ranging from basophils and mast cells to smooth muscle cells. The secondary functions of granzyme B are also numerous. Granzyme B has shown to be involved in inducing inflammation by stimulating cytokine release and is also involved in extracellular matrix remodeling. In embodiments, the modified cell has an enhanced migration capability in response to a chemokine as compared to a corresponding T cell that does not overexpress CDC42. In embodiments, the chemokine is CCL5. In embodiments, the modified cell comprises a polynucleotide encoding SEQ ID NO: 43 and the antigen binding molecule. In embodiments, the modified cell comprises a polynucleotide encoding SEQ ID NO: 43, the polynucleotide is present in the modified cell in a recombinant DNA construct, in an mRNA, or in a viral vector. In embodiments, the polynucleotide is regulated by a promoter comprising a binding site for a transcription modulator that modulates the expression of the CDC42 in the cell. In embodiments, the transcription modulator is or includes Hif1a, NFAT, FOXP3, and/or NFkB. Embodiments relate to an isolated nucleic acid comprising the polynucleotide.

Modified T-cells can be derived from a stem cell. The stem cells can be adult stem cells, embryonic stem cells, more particularly non-human stem cells, cord blood stem cells, progenitor cells, bone marrow stem cells, induced pluripotent stem cells, totipotent stem cells or hematopoietic stem cells. A modified cell can also be a dendritic cell, an NK-cell, a B-cell, or a T-cell selected from the group consisting of inflammatory T-lymphocytes, cytotoxic T-lymphocytes, regulatory T-lymphocytes or helper T-lymphocytes. In another embodiment, Modified cells can be derived from the group consisting of CD4+T-lymphocytes and CD8+T-lymphocytes. Prior to expansion and genetic modification of the cells of the invention, a source of cells can be obtained from a subject through a variety of non-limiting methods. T cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In embodiments, any number of T cell lines available and known to those skilled in the art can be used. In embodiments, modified cells can be derived from a healthy donor, from a patient diagnosed with cancer or from a patient diagnosed with an infection. In embodiments, modified cell is part of a mixed population of cells which present different phenotypic characteristics.

The term "stem cell" refers to any of certain type of cells which have the capacity for self-renewal and the ability to differentiate into other kinds of cells. For example, a stem cell gives rise either to two daughter stem cells (as occurs in vitro with embryonic stem cells in culture) or to one stem cell and a cell that undergoes differentiation (as occurs, e.g. in hematopoietic stem cells, which give rise to blood cells). Different categories of stem cells may be distinguished on the basis of their origin and/or the extent of their capacity for differentiation into other types of cells. For example, stem cells may include embryonic stem (ES) cells (i.e., pluripotent stem cells), somatic stem cells, Induced pluripotent stem cells, and any other types stem cells.

The pluripotent embryonic stem cells may be found in the inner cell mass of a blastocyst and have a high innate capacity for differentiation. For example, pluripotent embryonic stem cells may have the potential to form any type of cell in the body. When grown in vitro for long periods of time, ES cells maintain pluripotency: progeny cells retain the potential for multilineage differentiation.

Somatic stem cells include the fetal stem cells (from the fetus) and adult stem cells (found in various tissues, such as bone marrow). These cells have been regarded as having a capacity for differentiation lower than that of the pluripotent ES cells—with the capacity of fetal stem cells being greater than that of adult stem cells; they apparently differentiate into only a few types of cells and have been described as multipotent. The 'tissue-specific' stem cells normally give rise to only one type of cell. For example, embryonic stem cells may be differentiated into blood stem cells (e.g., Hematopoietic stem cells (HSCs)), which may be further differentiated into various blood cells (e.g., red blood cells, platelets, white blood cells).

Induced pluripotent stem cells (i.e., iPS cells or iPSCs) may include a type of pluripotent stem cell artificially derived from a non-pluripotent cell (e.g., an adult somatic cell) by inducing an expression of specific genes. Induced pluripotent stem cells are similar to natural pluripotent stem cells, such as embryonic stem (ES) cells, in many aspects, such as the expression of certain stem cell genes and proteins, chromatin methylation patterns, doubling time, embryoid body formation, teratoma formation, viable chimera formation, and potency and differentiability. Induced pluripotent cells can be made from adult stomach, liver, skin cells, and blood cells.

In embodiments, the two different antigen binding domains can be on a CAR, and a T cell receptor (TCR) and are encoded by separate nucleic acids. The binding domain of a TCR can target a specific tumor antigen or tumor marker on the cell of a tumor. In embodiments, the TCR binding domain is a TCR alpha binding domain or TCR beta binding domain that targets a specific tumor antigen. In embodiments, the TCR comprises the TCRγ and TCRδ chains or the TCRα and TCRβ chains. The present disclosure also describes vectors including the isolated nucleic acids described herein. In embodiments, a single vector contains the isolated nucleic acid encoding the first CAR and second CAR or TCR. In embodiments, a first vector contains the first nucleic acid encoding a first CAR, and a second vector contains the nucleic acid encoding the second CAR or TCR. In embodiments, the vector comprises a bispecific CAR including at least two antigen binding domains.

Lymphocyte or T cell response in a subject refers to cell-mediated immunity associated with a helper, killer, regulatory, and other types of T cells. For example, T cell response may include activities such as assisting other WBCs in immunologic processes and identifying and destroying virus-infected cells and tumor cells. T cell response in the subject can be measured via various indicators such as a number of virus-infected cells and/or tumor cells that T cells kill, the amount of cytokine that T cells release in co-culturing with virus-infected cells and/or tumor cells, a level of proliferation of T cells in the subject, a phenotype change of T cells, for example, changes to memory T cells, and a level longevity or lifetime of T cells in the subject.

In embodiments, the method of enhancing T cell response comprises treating a subject in need thereof, for example, a subject diagnosed with a tumor. The term tumor refers to a mass, which can be a collection of fluid, such as blood, or a solid mass. A tumor can be malignant (cancerous) or benign. Examples of blood cancers include chronic lymphocytic leukemia, acute myeloid leukemia, acute lymphoblastic leukemia, and multiple myeloma.

Solid tumors usually do not contain cysts or liquid areas. The major types of malignant solid tumors include sarcomas and carcinomas. Sarcomas are tumors that develop in soft tissue cells called mesenchymal cells, which can be found in blood vessels, bone, fat tissues, ligament lymph vessels, nerves, cartilage, muscle, ligaments, or tendon, while carcinomas are tumors that form in epithelial cells, which are found in the skin and mucous membranes. The most common types of sarcomas include undifferentiated pleomorphic sarcoma, which involves soft tissue and bone cells; leiomyosarcoma, which involves smooth muscle cells that line blood vessels, gastrointestinal tract, and uterus; osteosarcoma which involves bone cells, and liposarcoma which involves fat cells. Some examples of sarcomas include Ewing sarcoma, Rhabdomyosarcoma, chondosarcoma, mesothelioma, fibrosarcoma, fibrosarcoma, and glioma.

The five most common carcinomas include adrenocarcinoma which involves organs that produce fluids or mucous, such as the breasts and prostate; basal cell carcinoma which involves cells of the outer-most layer of the skin, for example, skin cancer; squamous cell carcinoma which involves the basal cells of the skin; and transitional cell carcinoma which affects transitional cells in the urinary tract which includes the bladder, kidneys, and ureter. Examples of carcinomas include cancers of the thyroid, breast, prostate, lung, intestine, skin, pancreas, liver, kidneys, and bladder, and cholangiocarcinoma.

The methods described herein can be used to treat a subject diagnosed with cancer. Cancer can be a blood cancer or can be a solid tumor, such as a sarcoma or carcinoma. The method of treating includes administering an effective amount of T cells comprising a first antigen binding domain and a second antigen binding domain to the subject to provide a T-cell response, wherein the first antigen binding domain binds a cell surface molecule of a WBC, and the second antigen binding domain binds an antigen different from the cell surface molecule of the WBC. In embodiments, enhancing the T cell response in the subject includes selectively enhancing proliferation of T cell expressing the first antigen binding domain and the second antigen binding domain in vivo.

In embodiments, the first antigen binding domain is on a CAR, and the second antigen binding domain is on a T Cell Receptor (TCR). In embodiments, the TCR is a modified TCR. In embodiments, the TCR is derived from spontaneously occurring tumor-specific T cells in patients. In embodiments, the TCR binds a tumor antigen. In embodiments, the tumor antigen comprises CEA, gp100, MART-1, p53, MAGE-A3, or NY-ESO-1.

In embodiments, a T cell clone that expresses a TCR with a high affinity for the target antigen may be isolated. Tumor-infiltrating lymphocytes (TILs) or PBMCs can be cultured in the presence of antigen-presenting cells (APCs) pulsed with a peptide representing an epitope known to elicit a dominant T cell response when presented in the context of a defined HLA allele. High-affinity clones may be then selected on the basis of MHC-peptide tetramer staining and/or the ability to recognize and lyse target cells pulsed with low titrated concentrations of cognate peptide antigen. After the clone has been selected, the TCRα and TCRβ chains or TCRγ and TCRβ chains are identified and isolated by molecular cloning. For example, for TCRα and TCRβ chains, the TCRα and TCRβ gene sequences are then used to generate an expression construct that ideally promotes stable, high-level expression of both TCR chains in human T cells. The transduction vehicle, for example, a gammaretrovirus or lentivirus, can then be generated and tested for functionality (antigen specificity and functional avidity) and used to produce a clinical lot of the vector. An aliquot of the final product can then be used to transduce the target T cell population (generally purified from patient PBMCs), which is expanded before infusion into the patient.

Various methods may be implemented to obtain genes encoding tumor-reactive TCR. More information is provided in Kershaw et al., Clin Transl Immunology. 2014 May; 3(5): e16. In embodiments, specific TCR can be derived from spontaneously occurring tumor-specific T cells in patients. Antigens included in this category include the melanocyte differentiation antigens MART-1 and gp100, as well as the MAGE antigens and NY-ESO-1, with expression in a broader range of cancers. TCRs specific for viral-associated malignancies can also be isolated, as long as viral proteins are expressed by transformed cells. Malignancies in this category include liver and cervical cancer, associated with hepatitis and papilloma viruses, and Epstein-Barr virus-associated malignancies. In embodiments, target antigens of the TCR may include CEA (e.g., for colorectal cancer), gp100, MART-1, p53 (e.g., for Melanoma), MAGE-A3 (e.g., Melanoma, esophageal and synovial sarcoma), NY-ESO-1 (e.g., for Melanoma and sarcoma as well as Multiple myelomas).

In embodiments, preparation and transfusion of tumor infiltrating lymphocytes (TIL) may be implemented by the following. For example, tumor tissue from surgical or biopsy specimens can be obtained under aseptic conditions and transported to the cell culture chamber in the ice box. Necrotic tissue and adipose tissue can be removed. The tumor tissue may be cut into small pieces of about 1-3 cubic millimeters. Collagenase, hyaluronidase, and DNA enzyme can be added and digested overnight at 4° C. Filtering with 0.2 μm filter, cells can be separated and collected by lymphocyte separation fluid, 1500 rpm for 5 min. Expanding the cells with a culture medium comprising PHA, 2-mercaptoethanol, and CD3 monoclonal antibody, a small dose of IL-2 (10-20 IU/ml) can be added to induce activation and proliferation. According to the growth situation, the cell density can be carefully detected and maintained within the range of $0.5$-$2\times10^6$/ml under the condition of 37° C. and 5% CO2 for 7-14 days. TIL positive cells have the ability to kill homologous cancer cell may be screened out by co-culture. The positive cells can be amplified in a serum-free medium containing a high dose of IL2 (5000-6000 IU/ml) until greater than $1\times10^{11}$ TILs can be obtained. To administer TILs, they may be first collected in saline solution using continuous-flow centrifugation and then filtered through a platelet-administration set into a volume of 200-300 ml containing 5% albumin and 450 000 IU of IL-2. The TILs may be infused into patients through a central venous catheter over a period of 30-60 minutes. In embodiments, TILs may be infused in two to four separate bags; the infusions may be separated by several hours.

In embodiments, the isolated T cell comprises a dominant negative variant of a receptor of programmed death 1 (PD-1), cytotoxic T lymphocyte antigen-4 (CTLA-4), B- and T-lymphocyte attenuator (BTLA), T cell immunoglobulin mucin-3 (TIM-3), lymphocyte-activation protein 3 (LAG-3), T cell immunoreceptor with Ig and ITIM domains (TIGIT), leukocyte-associated immunoglobulin-like receptor 1 (LAIRD, natural killer cell receptor 2B4 (2B4), or CD 160. In embodiments, the isolated T cell comprises a reduced amount of TCR, as compared to the corresponding wide-type T cell. Dominant negative mutations have an altered gene product that acts antagonistically to the wild-type allele. These mutations usually result in an altered molecular function (often inactive) and are characterized by a dominant or semi-dominant phenotype.

The present disclosure describes pharmaceutical compositions. The pharmaceutical compositions include one or more of the following: CAR molecules, TCR molecules, modified CAR T cells, modified cells comprising CAR or TCR, modified cells, nucleic acids, and vectors described herein. Pharmaceutical compositions are administered in a manner appropriate to the patient based on disease being treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "a tumor-inhibiting effective amount", or "therapeutic amount" is indicated, the precise amount of the compositions of the present disclosure to be administered can be determined by a physician with consideration of individual differences in age, weight, tumor size, extent of infection or metastasis, and condition of the patient (subject). It can be stated that a pharmaceutical composition comprising the T cells described herein may be administered at a dosage of $10^4$ to $10^9$ cells/kg body weight, preferably $10^9$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly. In certain embodiments, it may be desired to administer activated T cells to a subject and then subsequently redraw the blood (or have apheresis performed), collect the activated and expanded T cells, and reinfuse the patient with these activated and expanded T cells. This process can be carried out multiple times every few weeks. In certain embodiments, T cells can be activated from blood draws from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocols, may select out certain populations of T cells.

The administration of the pharmaceutical compositions described herein may be carried out in any convenient manner, including by aerosol inhalation, injection, ingestion, transfusion, implantation, or transplantation. The compositions described herein may be administered to a patient subcutaneously, intradermally, intratumorally, intranodally, intramedullary, intramuscularly, by intravenous (i. v.) injection, or intraperitoneally. In embodiments, the T cell compositions described herein are administered to subjects by intradermal or subcutaneous injection. In embodiments, the T cell compositions of the present disclosure are administered by i.v. injection. The compositions of T cells may be injected directly into a tumor, lymph node, or site of infection. In embodiments, cells activated and expanded using the methods described herein, or other methods known in the art where T cells are expanded to therapeutic levels, are administered to patients in conjunction with (e.g., before, simultaneously or following) any number of relevant treatment modalities, including but not limited to treatment with agents for antiviral therapy, cidofovir and interleukin-2, Cytarabine (also known as ARA-C); or natalizumab treatment for MS patients; or efalizumab treatment for psoriasis patients or other treatments for PML patients. In further embodiments, the T cells described herein can be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun 73:316-321, 1991; Bierer et al., Curr. Opin. Immun 5:763-773, 1993; Isoniemi (supra)). In embodiments, the cell compositions described herein are administered to a subject in conjunction with (e.g., before, simultaneously or following) bone marrow transplantation, T cell ablative therapy using either chemotherapy agents such as fludarabine, external-beam radiation therapy (XRT), cyclophosphamide, or antibodies such as OKT3 or CAMPATH. In embodiments, the cell compositions described herein are administered following B-cell ablative therapy. For example, agents that react with CD20, e.g., Rituxan may be administered to patients. In embodiments, subjects may undergo standard treatment with high dose chemotherapy followed by peripheral blood stem cell transplantation. In certain embodiments, following the transplant, subjects receive an infusion of the expanded immune cells of the present disclosure. In embodiments, expanded cells are administered before or following surgery.

In embodiments, CpG oligonucleotides (e.g., Class B CpG oligonucleotides) can be systemically and repeatedly administered to a subject to enhance anti-tumor effect of the pharmaceuticals described herein (e.g., CAR T cells) by introducing macrophage activation. For example, the administration of CAR T cells and CpG oligonucleotides can be combined to treat a subject having a solid tumor. Information on administration of CpG oligonucleotides may be found at Nat Immunol. 2019 March; 20(3): 265-275, which is incorporated by reference in its entirety.

The dosage of the above treatments to be administered to a subject in need thereof will vary with the precise nature of the condition being treated and the recipient of the treatment. The scaling of dosages for human administration can be performed according to art-accepted practices by a physician depending on various factors.

Additional information on the methods of cancer treatment using engineered or modified T cells is provided in U.S. Pat. No. 8,906,682, incorporated by reference in its entirety.

Embodiments described herein relate to an in vitro method for preparing modified cells. The method may include obtaining a sample of cells from a subject. For example, the sample may include T cells or T cell progenitors. The method may further include transfecting the sample of cells with a DNA encoding at least a CAR and culturing the population of CAR cells ex vivo in a medium that selectively enhances proliferation of CAR-expressing T cells.

In embodiments, the sample is a cryopreserved sample. In embodiments, the sample of cells is from umbilical cord blood or a peripheral blood sample from the subject. In embodiments, the sample of cells is obtained by apheresis or venipuncture. In embodiments, the sample of cells is a subpopulation of T cells.

The present disclosure is further described by reference to the following exemplary embodiments and examples. These exemplary embodiments and examples are provided for purposes of illustration only and are not intended to be limiting unless otherwise specified. Thus, the present disclosure should in no way be construed as being limited to the following exemplary embodiments and examples, but rather, should be construed to encompass any and all variations which become evident as a result of the teaching provided herein.

EXEMPLARY EMBODIMENTS

The following are exemplary embodiments:
1. An isolated nucleic acid sequence comprising a nucleic acid sequence and an additional nucleic acid sequence, the nucleic acid sequence encoding an antigen binding molecule, the additional nucleic acid sequence being associated with a disruption in an endogenous gene or encoding at least one of LRCH1, DOCK8, and Cdc42.
2. A modified cell comprising: an antigen binding molecule; and:
   a disruption in an endogenous gene, or
   an addition of exogenous gene that is associated with a biosynthesis or transportation pathway of at least one of LRCH1, DOCK8, and Cdc42, wherein the modified cell has an increased amount of DOCK8 or Cdc42 and/or a reduced amount of LRCH1 as compared with a corresponding wild type cell.
3. The modified cell of embodiment 2, wherein the modified T cell has a disruption in an endogenous gene associated with a biosynthesis or transportation pathway of LRCH1.
4. The modified cell of embodiment 3, further comprising a TALEN targeting SEQ ID NO: 24.
5. The modified cell of embodiment 3, wherein the TALEN comprises a left arm comprising SEQ ID NO: 34 and a right arm comprising SEQ ID NO: 35.
6. The modified cell of embodiment 3, further comprising a ZFN targeting SEQ ID NO: 23.
7. The modified cell of embodiment 3, wherein the ZFN comprises a left arm comprising one of the nucleic acid sequences of SEQ ID NOs: 26-29 and a right arm comprising one of the nucleic acid sequences of SEQ ID NOs: 30-33.
8. The modified cell of embodiment 2, wherein DOCK8 or Cdc42 is overexpressed as compared to the corresponding wild type cell.
9. The modified cell of embodiment 2, wherein a level of expression of DOCK8 or Cdc42 is greater than the average level of expression of DOCK8 or Cdc42 on the cell by at least about 10%, 20%, 30%, 40%, or 50%.
10. The modified cell of embodiment 2, wherein the genome of the cell comprises a polynucleotide sequence encoding the DOCK8 or Cdc42, the polynucleotide sequence operably linked to a promoter polynucleotide sequence.
11. The modified cell of embodiment 2, wherein the modified cell is a lymphocyte, leukocyte, or PBMC.
12. A pharmaceutical composition comprising a population of the modified cells of any of embodiments 2-11.
13. A method of causing or eliciting a T cell response in a subject in need thereof and/or treating a tumor of the subject, the method comprising administering an effective amount of the composition of embodiment 12 to the subject.
14. The isolated nucleic acid sequence, the modified cell, or the method of any one of embodiments 1-11, wherein the binding molecule is a CAR that comprises an extracellular domain, a transmembrane domain, and an intracellular domain, and the extracellular domain binds an antigen.
15. The isolated nucleic acid sequence, the modified cell, or the method of embodiment 14, wherein the intracellular domain comprises a costimulatory signaling region that comprises an intracellular domain of a costimulatory molecule selected from the group consisting of CD27, CD28, 4-1BB, OX40, CD30, CD40, PD-1, ICOS, lymphocyte function-associated antigen-1 (LFA-1), CD2, CD7, LIGHT, NKG2C, B7-H3, and any combination thereof.
16. The isolated nucleic acid sequence, the modified cell, or the method of embodiment 15, wherein the antigen is Epidermal growth factor receptor (EGFR), Variant III of the epidermal growth factor receptor (EGFRvIII), Human epidermal growth factor receptor 2 (HER2), Mesothelin (MSLN), Prostate-specific membrane antigen (PSMA), Carcinoembryonic antigen (CEA), Disialoganglioside 2 (GD2), Interleukin-13Ra2 (IL13Ra2), Glypican-3 (GPC3), Carbonic anhydrase IX (CAIX), L1 cell adhesion molecule (L1-CAM), Cancer antigen 125 (CA125), Cluster of differentiation 133 (CD133), Fibroblast activation protein (FAP), Cancer/testis antigen 1B (CTAG1B), Mucin 1 (MUC1), Folate receptor-α (FR-α), CD19, FZD10, TSHR, PRLR, Muc 17, GUCY2C, CD207, CD3, CD5, B-Cell Maturation Antigen (BCMA), or CD4.
17. The isolated nucleic acid sequence, the modified cell, or the method of any one of embodiments 2-16, wherein the modified cell comprises a dominant negative PD-1 mutant such that PD-1/PDl-1 signaling pathway of the cell is interfered.
18. The isolated nucleic acid sequence, the modified cell, or the method of any one of embodiments 2-17, wherein the DOCK8 or Cdc42 is present in the modified cell in a recombinant DNA construct, in an mRNA, or in a viral vector.
19. The isolated nucleic acid sequence, the modified cell, or the method of any one of embodiments 2-18, wherein the modified cell comprises a DOCK8 or Cdc42 mRNA encoding the DOCK8 or Cdc42, and the mRNA is not integrated into the genome of the modified cell.
20. The isolated nucleic acid sequence, the modified cell, or the method of any one of embodiments 2-19, wherein the modified cell comprises a nucleic acid sequence comprising or the isolated nucleic acid sequence comprises a promoter comprising a binding site for a transcription modulator that modulates expression of a therapeutic agent in the cell.
21. The isolated nucleic acid sequence, the modified cell, or the method of embodiment 20, wherein the transcription modulator is or includes Hif1a, NFAT, FOXP3, and/or NFkB.
22. The isolated nucleic acid sequence, the modified cell, or the method of embodiment 21, wherein the promoter is responsive to the transcription modulator.

23. The isolated nucleic acid sequence, the modified cell, or the method of embodiment 22, wherein the promoter is operably linked to the nucleic acid sequence encoding the therapeutic agent such that the promoter drives expression of the therapeutic agent in the cell.

24. A cell modified to express one or more molecules at a level that is higher or lower than the level of the one or more molecules expressed by a cell that has not been modified to express the one or more molecules, wherein the one or more molecules are associated with cell migration.

25. A modified cell engineered to express an antigen binding molecule, wherein expression and/or function of one or more molecules in the modified cell has been enhanced or reduced, and wherein the one or more molecules are associated with cell migration.

26. The modified cell of any one of embodiments 24 or 25, wherein the modified cell comprises: a disruption in an endogenous gene, or
    an addition of exogenous gene that is associated with a biosynthesis or transportation pathway of the one or more molecules.

27. A method or use of polynucleotide, the method comprising
    providing a viral particle (e.g., AAV, lentivirus or their variants) comprising a vector genome, the vector genome comprising the polynucleotide encoding the one more molecules and a polynucleotide encoding a binding molecule, the polynucleotide operably linked to an expression control element conferring transcription of the polynucleotides; and
    administering an amount of the viral particle to a subject such that the polynucleotide encoding the binding molecule is expressed in the subject, where the one or more molecules are associated with cell migration.

28. The method of embodiment 27, wherein the AAV preparation may include AAV vector particles, empty capsids, and host cell impurities, thereby providing an AAV product substantially free of AAV empty capsids.

29. A pharmaceutical composition comprising a population of the cells of any one of embodiments 24-26.

30. A method of causing or eliciting T cell response in a subject in need thereof and/or treating a tumor of the subject, the method comprising administering an effective amount of the composition of embodiment 29 to the subject.

31. An isolated nucleic acid sequence encoding one or more molecules that are associated with cell migration.

32. The isolated nucleic acid sequence, modified cell, method, or pharmaceutical composition of any one of embodiments 24-31, wherein the one or more molecules comprise at least one of DOCK8, CDC42, and LRCH1, a functional variant of the one or more molecules, or a functional fragment of the one or more molecules.

33. The isolated nucleic acid sequence, modified cell, method, or pharmaceutical composition of any one of embodiments 24-32, wherein the one or more molecules are or comprise CDC42, which is overexpressed in the modified T cells.

34. The isolated nucleic acid sequence, modified cell, method, or pharmaceutical composition of any one of embodiments 24-33, wherein the one or more molecules are or comprise LRCH1 of which expression is reduced in the modified T cells.

35. The isolated nucleic acid sequence, modified cell, method, or pharmaceutical composition of any one of embodiments 24-34, wherein the modified cell comprises a recombinant polynucleotide encoding the SEQ ID NOS: 43 and/or 39.

36. The modified cell of any one of the preceding embodiments, wherein the modified cell comprises an antigen binding molecule, wherein a chimeric antigen receptor (CAR) comprises the antigen binding molecule, and wherein the CAR comprises an antigen-binding domain, a transmembrane domain, and an intracellular signaling domain.

37. The modified cell of embodiment 36, wherein the antigen-binding domain binds to a tumor antigen selected from the group consisting of: TSHR, CD19, CD123, CD22, CD30, CD171, CS-1, CLL-1, CD33, EGFRvIII, GD2, GD3, BCMA, Tn Ag, PSMA, ROR1, FLT3, FAP, TAG72, CD38, CD44v6, CEA, EPCAM, B7H3, KIT, IL-13Ra2, Mesothelin, IL-11Ra, PSCA, PRSS21, VEGFR2, LewisY, CD24, PDGFR-beta, SSEA-4, CD20, Folate receptor alpha, ERBB2 (Her2/neu), MUC1, EGFR, NCAM, Prostase, PAP, ELF2M, Ephrin B2, IGF-I receptor, CAIX, LMP2, gp100, bcr-abl, tyrosinase, EphA2, Fucosyl GM1, sLe, GM3, TGSS, HMWMAA, o-acetyl-GD2, Folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, survivin and telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, Androgen receptor, Cyclin 61, MYCN, RhoC, TRP-2, CYP161, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, and IGLL1.

38. The modified cell of embodiment 36 and 37, wherein the intracellular signaling domain comprises a co-stimulatory signaling domain, or a primary signaling domain and a co-stimulatory signaling domain, wherein the co-stimulatory signaling domain comprises a functional signaling domain of a protein selected from the group consisting of CD27, CD28, 4-166 (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11 d, ITGAE, CD103, ITGAL, CD11a, LFA-1, ITGAM, CD11 b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D 39. The modified cell of any one of embodiments 24-30 or 31-35, wherein the modified cell comprises the antigen binding molecule, and a modified TCR comprises the antigen binding molecule.

40. The modified cell of embodiment 39, wherein the TCR is derived from spontaneously occurring tumor-specific T cells in patients.

41. The modified cell of embodiment 40, wherein the TCR binds a tumor antigen.

42. The modified cell of embodiment 41, wherein the tumor antigen comprises CEA, gp100, MART-1, p53, MAGE-A3, or NY-ESO-1.

43. The modified cell of embodiment 41, wherein the TCR comprises TCRγ and TCRδ chains, or TCRα and TCRβ chains, or a combination thereof.

44. The modified cell of any one of the preceding embodiments, wherein the cell is an immune effector cell. (e.g., a population of immune effector cells).

45. The modified cell of embodiment 44, wherein the immune effector cell is a T cell or an NK cell.

46. The modified cell of embodiment 45, wherein the immune effector cell is a T cell.

47. The modified cell of embodiment 45, wherein the T cell is a CD4+ T cell, a CD8+ T cell, or a combination thereof.

48. The modified cell of any one of the preceding embodiments, wherein the cell is a human cell.

49. The modified cell of any one of the preceding embodiments, wherein the enhanced expression and/or function of the one or more molecules are implemented by introducing a nucleic acid sequence encoding the one or more molecules and/or the binding molecule, which is present in the modified cell in a recombinant DNA construct, in an mRNA, or in a viral vector.

50. The modified cell of embodiment 49, wherein the nucleic acid sequence is an mRNA, which is not integrated into the genome of the modified cell.

51. The modified cell of embodiment 49, wherein the nucleic acid sequence is associated with an oxygen-sensitive polypeptide domain.

52. The modified cell of embodiment 51, wherein the oxygen-sensitive polypeptide domain comprises HIF VHL binding domain.

53. The modified cell of embodiment 49, wherein the nucleic acid sequence is regulated by a promoter comprising a binding site for a transcription modulator that modulates the expression of the CDC42 in the cell.

54. The modified cell of embodiment 53, wherein the transcription modulator is or includes Hif1a, NFAT, FOXP3, and/or NFkB.

55. A pharmaceutical composition comprising a population of the cells of any one of embodiments 1-54.

56. A method of causing or eliciting T cell response in a subject in need thereof and/or treating a tumor of the subject, the method comprising administering an effective amount of the composition of embodiment 55 to the subject.

EXAMPLES

Cells Expressing Chimeric Receptors

Lentiviral vectors that encode individual CAR molecules were generated and transfected with T cells, which are elaborated below. Techniques related to cell cultures, construction of cytotoxic T-lymphocyte assay may be found in "Control of large, established tumor xenografts with genetically retargeted human T cells containing CD28 and CD137 domains," PNAS, Mar. 3, 2009, vol. 106 no. 9, 3360-3365 and "Chimeric Receptors Containing CD137 Signal Transduction Domains Mediate Enhanced Survival of T Cells and Increased Antileukemic Efficacy In Vivo," Molecular Therapy, August 2009, vol. 17 no. 8, 1453-1464, which are incorporated herein by reference in its entirety. Corresponding sequences can be found in Table 1B.

TABLE 1B

Sequences and Identifiers

| SEQ ID | Identifier |
|---|---|
| 1 | SP |
| 2 | Linker |
| 3 | 4-1BB |
| 4 | CD3-zeta |
| 5 | WT CD3-zeta-aa |
| 6 | Hinge & TM domain |
| 7 | scFv CD19 |
| 8 | scFv Humanized CD19 |
| 9 | scFv FZD10 |
| 10 | scFv TSHR |
| 11 | scFv PRLR |
| 12 | scFv Muc 17 |
| 13 | scFv GUCY2C |
| 14 | scFv CD207 |
| 15 | Prolactin (ligand) |
| 16 | scFv CD3 |
| 17 | scFv CD4 |
| 18 | scFv CD4 |
| 19 | scFv CD5 |
| 20 | ScFv MUC1-5e5 |
| 21 | ScFv MUC1-Panko |
| 22 | LRCH1 |
| 23 | Target for ZFN |
| 24 | Target for Talen |
| 25 | Target for Crisper/Cas9 |
| 26 | ZFN Left F1 |
| 27 | ZFN Left F2 |
| 28 | ZFN Left F3 |
| 29 | ZFN Left F4 |
| 30 | ZFN Right F1 |
| 31 | ZFN Right F2 |
| 32 | ZFN Right F3 |
| 33 | ZFN Right F4 |
| 34 | Left arm TALEN |
| 35 | Left arm TALEN |
| 36 | Spacer |
| 37 | Sh-RNA-SCREMBLE: |
| 38 | Lrch1-shRNA1: |
| 39 | scFv GUCY2C: 5F9 Nucleotide Sequence |
| 40 | P2A |
| 41 | CD8hinge |
| 42 | CDC42 Nucleotide |
| 43 | CDC42 aa |
| 44 | 5F9-CD8hinge-41bb-CD3Z: Nucleotide |
| 45 | 5F9-CD8hinge-41bb-CD3Z: aa |
| 46 | 5F9-CD8hinge-41bb-CD3Z-P2A-CDC42: Nucleotide |
| 47 | 5F9-CD8hinge-41bb-CD3Z-P2A-CDC42: Aa |

CAR T Cells Overexpressing CDC42

Figure 2:
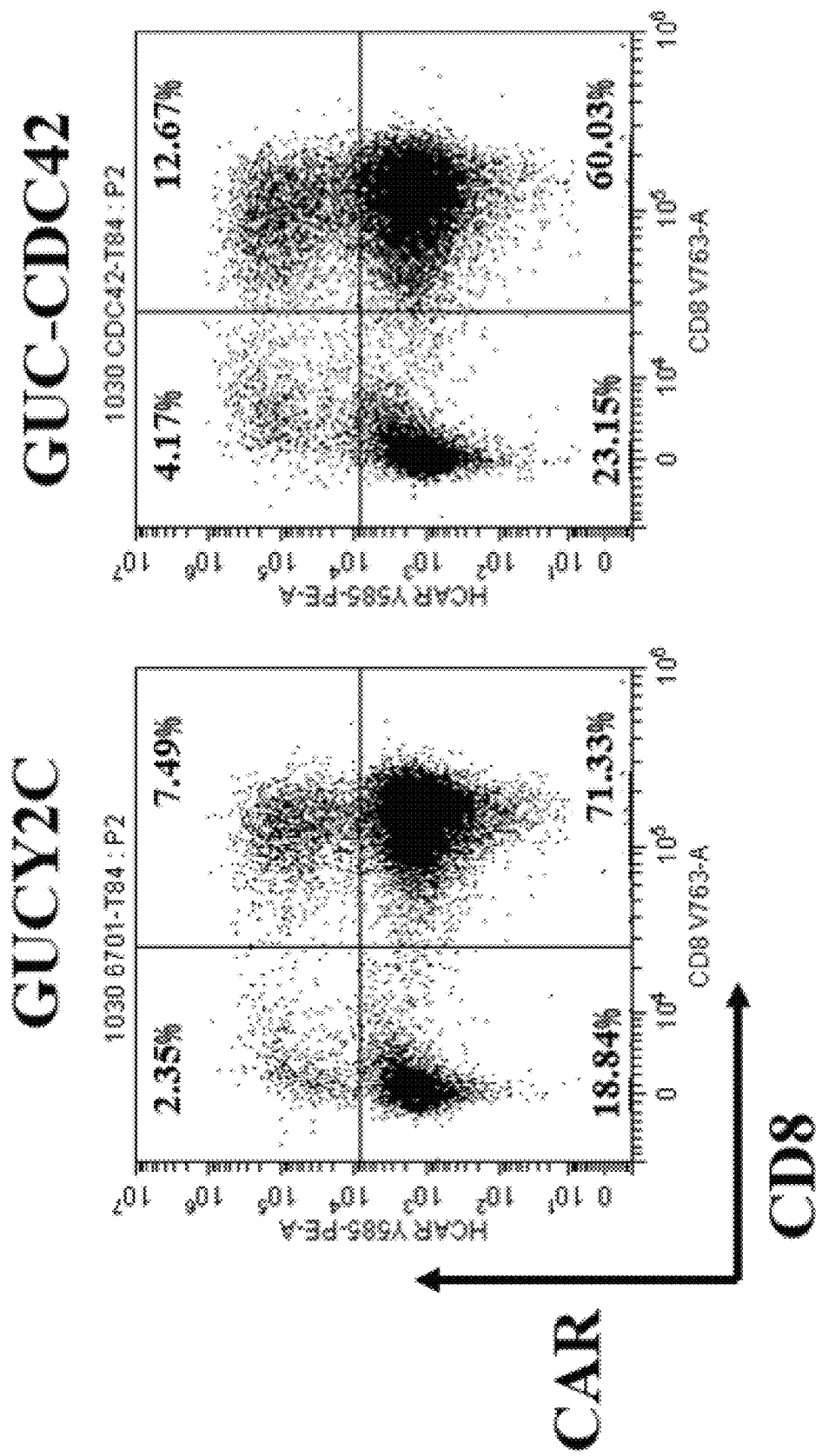
FIG. 2 shows cytometry assay results indicating that CDC42 sequence does not affect the expression of CAR on T cells.
Figure 3:
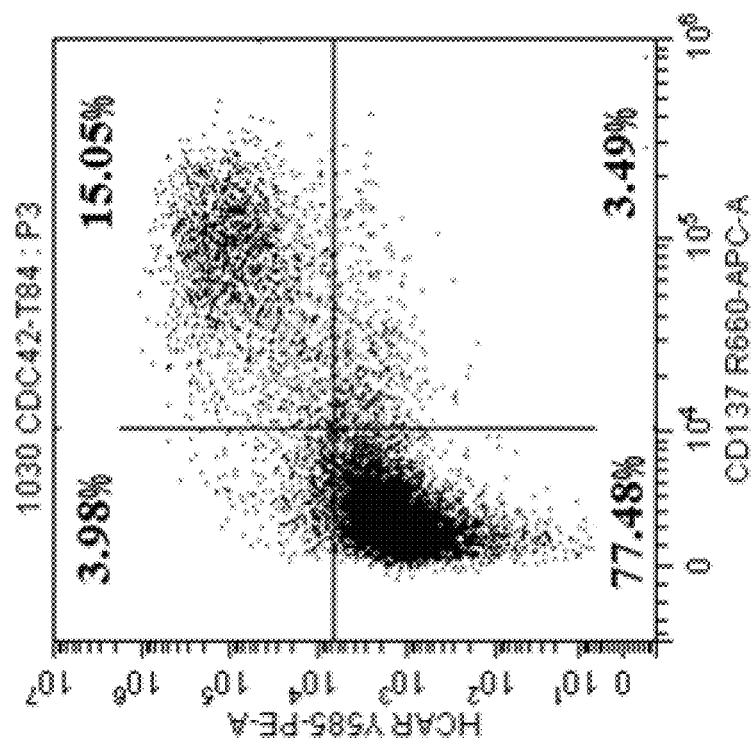
FIG. 3 shows cytometry assay results indicating that CDC42 sequence does not affect the activation of CAR T cells.
Figure 3:
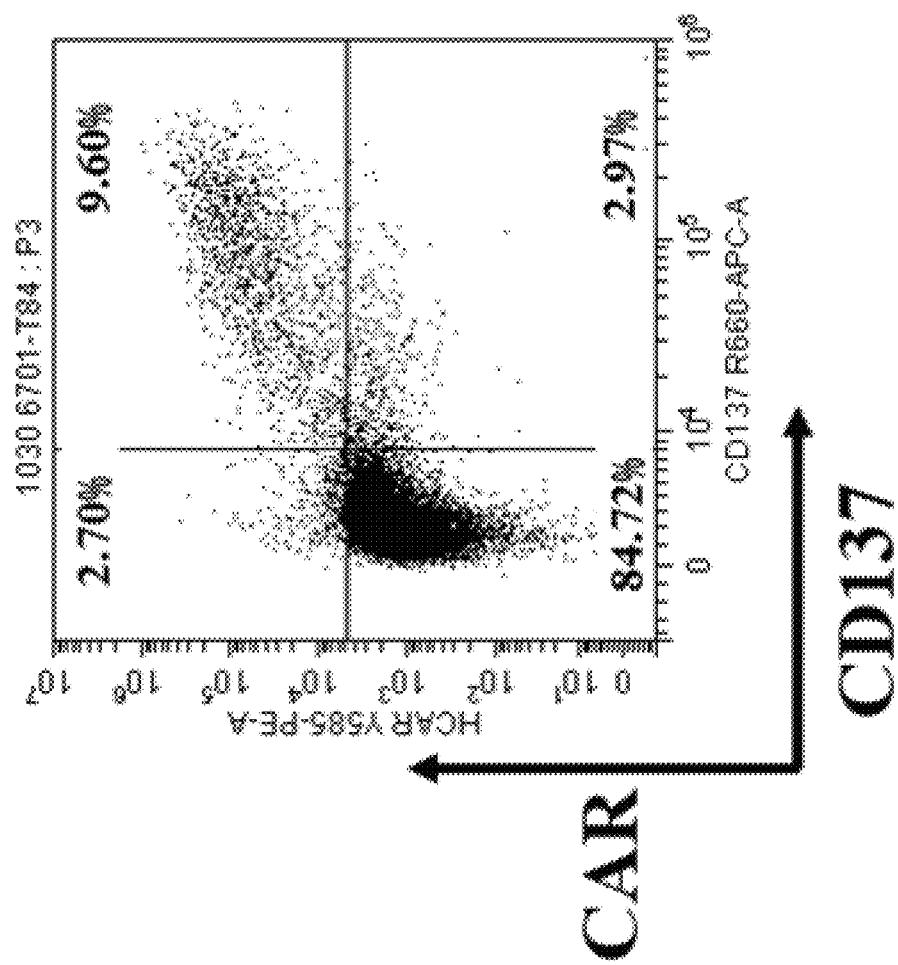
Figure 4:
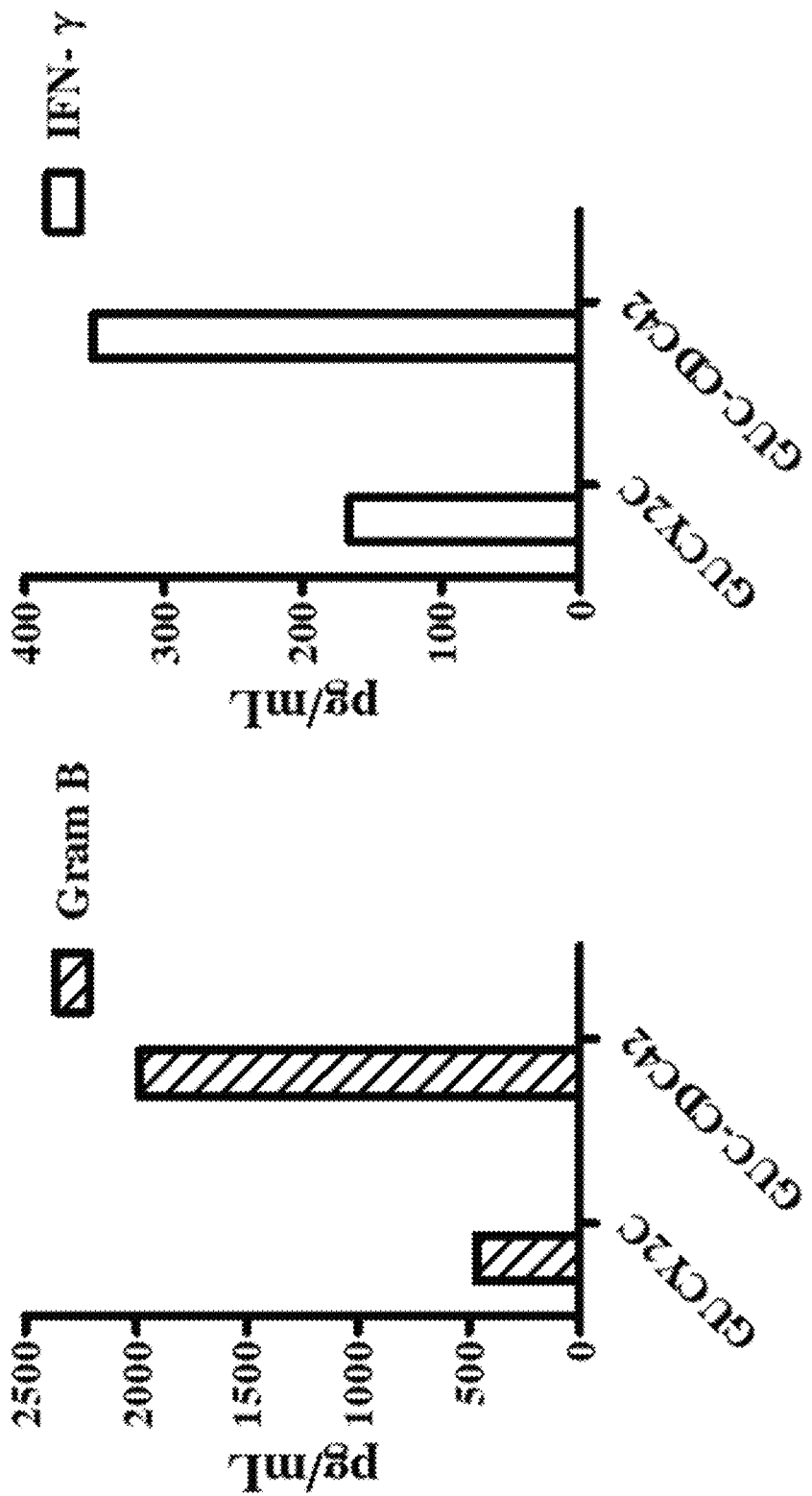
FIG. 4 shows CDC42 expression enhances the release of Gram B and IFN-γ after CAR activation.
Figure 5:
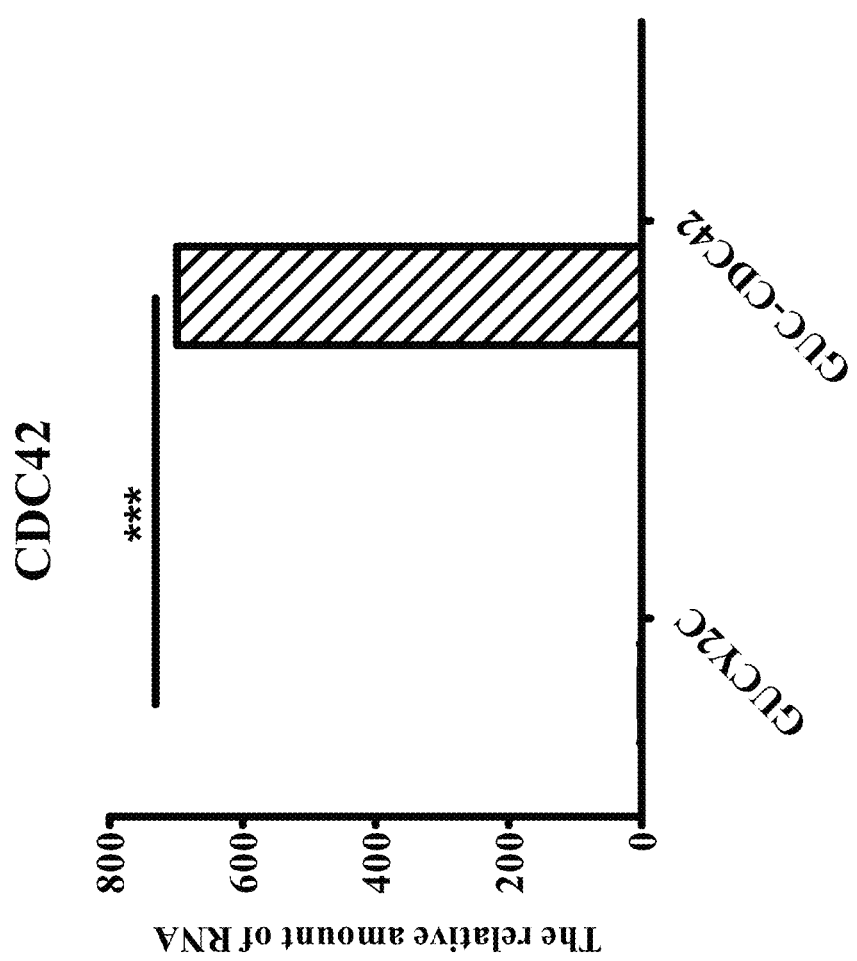
FIG. 5 shows that CDC42 was successfully expressed in CAR T cells.

PBMCs were obtained from volunteers, and T cells were selected on Day 1. The T cells were introduced with a vector containing GUCY2C CAR and a vector containing GUCY2C CAR-CDC42, respectively (See Table 2). The infected T cells were cultured until Day 7. On Day 7, $2 \times 10^5$ T84 cells were plated onto 24-well plates. On Day 8, $8 \times 10^5$ GUCY2C CAR T cells, and GUCY2C CAR-CDC42 T cells were removed and added to T84-coated 24-well plates. After coculturing for 24 hours, $3 \times 10^5$ cells were removed to determine the phenotype, and the supernatant was removed to determine the release of GRAM B and IFN-γ. The phenotype was determined using a flow cytometry assay. FIG. 2 shows cytometry assay results indicating that CDC42 sequence does not affect the expression of CAR on T cells. FIG. 3 shows cytometry assay results indicating that CDC42 sequence does not affect the activation of CAR T cells. FIG. 4 shows CDC42 expression enhances the release of GRAM B and IFN-γ after CAR activation. qPCR was used to verify the efficiency of overexpressing CDC42. FIG. 5 shows that CDC42 was successfully expressed in CART cells. On Day 7, 2×10⁶ GUCY2C CART cells, and GUCY2C CAR-CDC42 cells were used to verify the efficiency of overexpressing CDC42, respectively. RNA was extracted using TRAzol, reverse transcription was performed using this RNA as a template, and qPCR was performed using reverse transcript as a template to measure the overexpression of CDC42.

TABLE 2

| ID | Construct structure |
|---|---|
| GUCY2C | 5F9-CD8hinge-41BB-CD3Z |
| GUC-CDC42 | 5F9-CD8hinge-41BB-CD3Z-P2A-CDC42 |
| GUCY2C | 5F9-CD8hinge-41BB-CD3Z |
| GUC-SCR | U6-shRNA-Scremble-5F9-CD8hinge-41BB-CD3Z |
| ShRNA1 | U6-shRNA-1-5F9-CD8hinge-41BB-CD3Z |

Overexpression CDC42 Enhance CAR T Cells' Migration Ability

Figure 6:
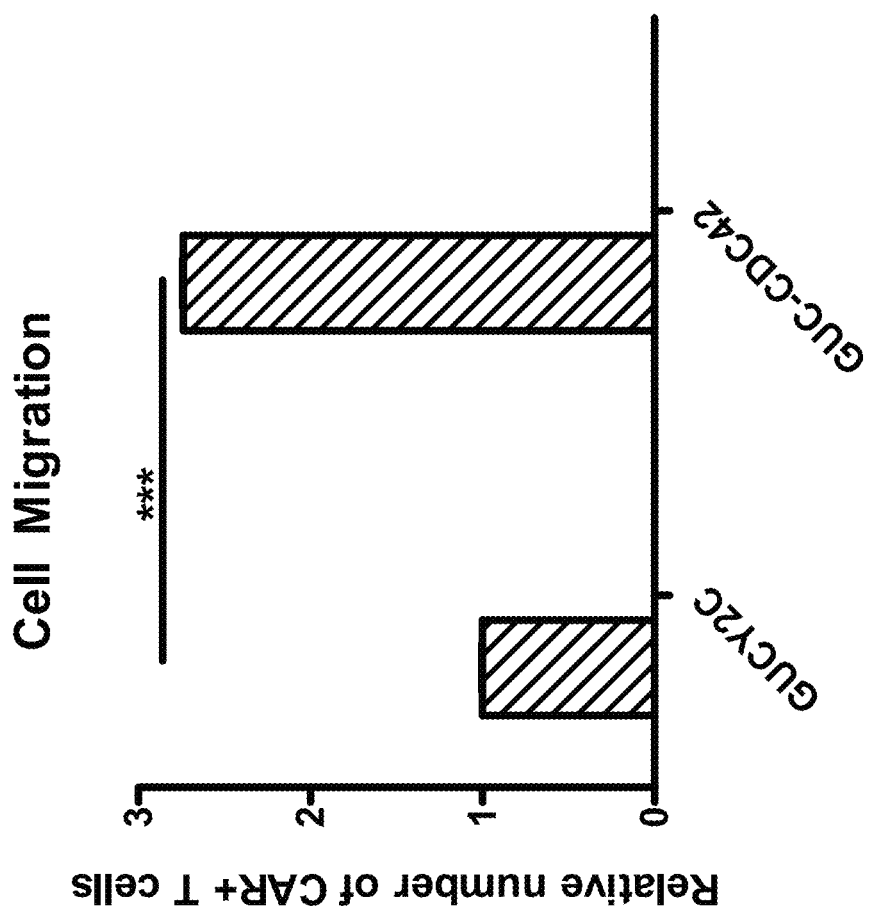
FIG. 6 shows that the migration ability of GUCY2C CART cells expressing CDC42 was significantly stronger than that of the control group.

The effect of overexpressing CDC42 on cell migration ability was verified by Transwell assay. On Day 9, 2×10⁵ GUCY2C CAR T cells and GUCY2C CAR-CDC42 cells were placed in separate Transwell upper chamber. 600 ul of X-VIVO containing 50 ng/ml CCL5 was placed in each of the Transwell lower chamber. Flow cytometry assay was performed after 4 hours to measure the number of CAR+ cells that migrated in the underlying medium. FIG. 6 shows that the migration ability of GUCY2C CAR T cells expressing CDC42 was significantly stronger than that of the control group.

CAR T Cells Overexpressing LRCH1 and Enhanced Cytokine Releases

Figure 7:
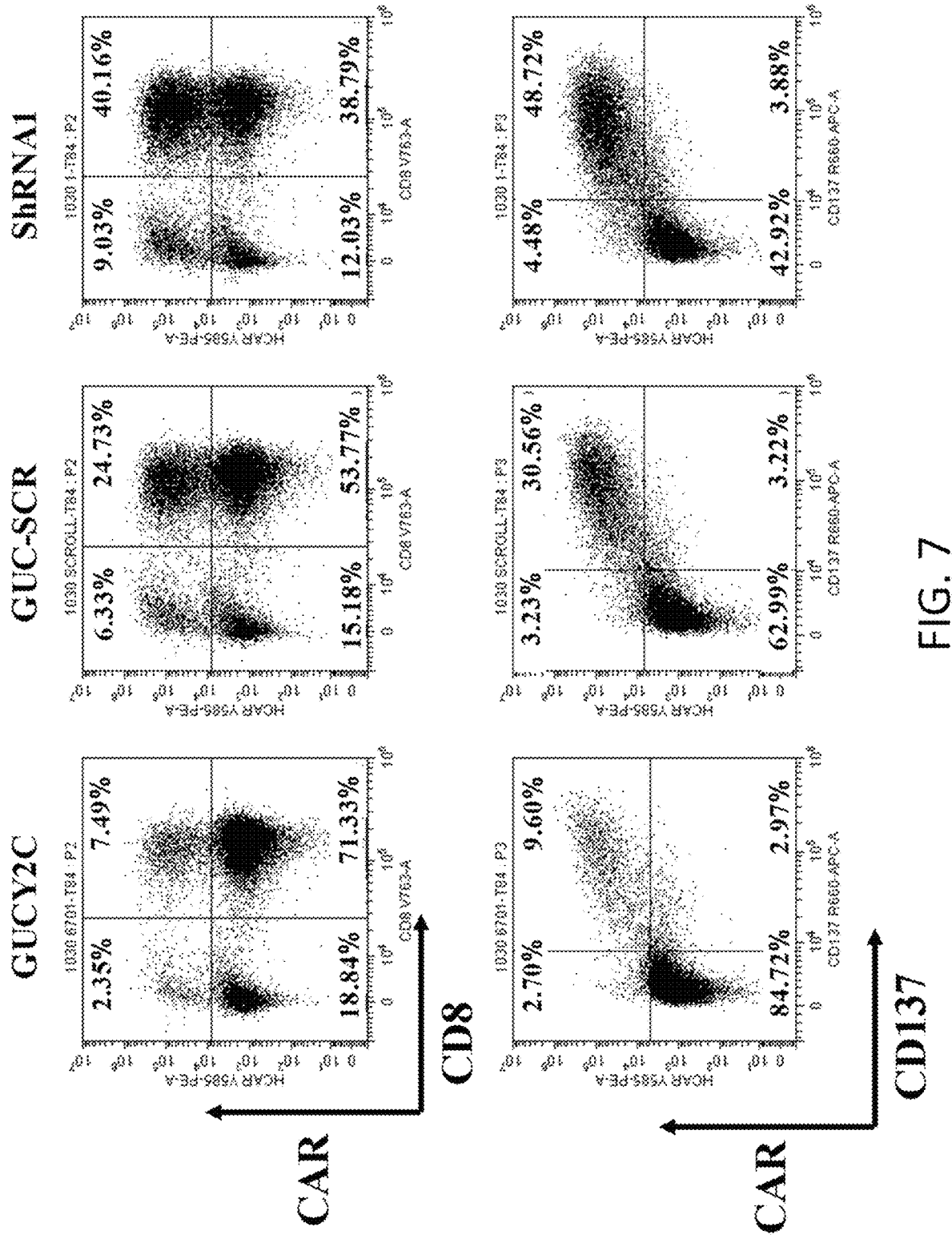
FIG. 7 shows cytometry assay results indicating that ShRNA1 sequence does not affect the expression of CAR on T cells and also shows cytometry assay results indicating that ShRNA1 sequence does not affect the activation of CAR T cells.
Figure 8:
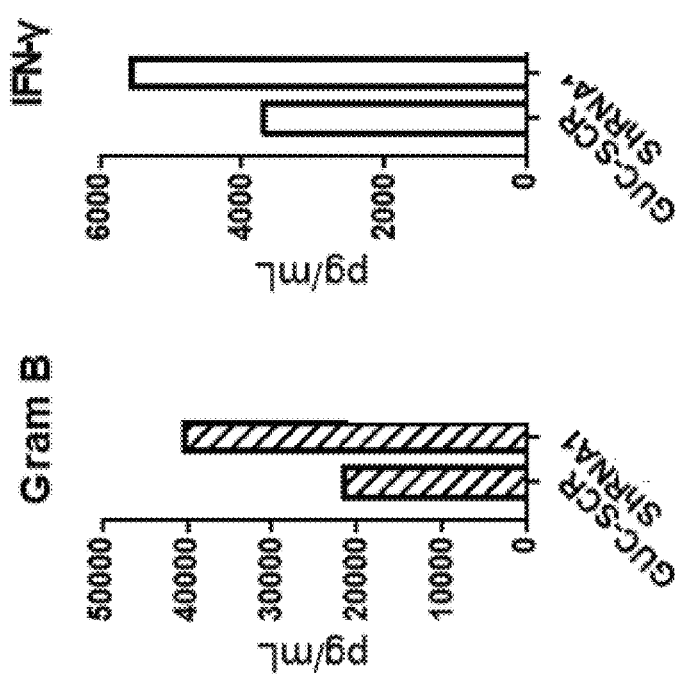
FIG. 8 shows ShRNA1 expression enhances the release of Gram B and IFN-γ.

PBMCs were obtained from volunteers, and T cells were selected on Day 1. The T cells were introduced with a vector containing GUC-SCR and a vector containing ShRNA1, respectively (See Table 2). The infected T cells were cultured until Day 7. On Day 7, 2×10⁵ T84 cells were plated onto 24-well plates. On Day 8, 8×10⁵ GUC-SCR CART cells and ShRNA1 CAR T cells were removed and added to T84-coated 24-well plates. After coculturing for 24 hours, 3×10⁵ cells were removed to determine the phenotype, and the supernatant was removed to determine the release of GRAM B and IFN-γ. The phenotype was determined using flow cytometry assay. FIG. 7 shows cytometry assay results indicating that ShRNA1 sequence does not affect the expression of CAR on T cells. FIG. 7 also shows cytometry assay results indicating that ShRNA1 sequence does not affect the activation of CAR T cells. FIG. 8 shows ShRNA1 expression enhances the release of GRAM B and IFN-γ after CAR activation. qPCR was used to verify the efficiency of overexpressing CDC42.

All publications, patents and patent applications cited in this specification are incorporated herein by reference in their entireties as if each individual publication, patent or patent application were specifically and individually indicated to be incorporated by reference. While the foregoing has been described in terms of various embodiments, the skilled artisan will appreciate that various modifications, substitutions, omissions, and changes may be made without departing from the spirit thereof.

The invention claimed is:

1. A modified T cell comprising a polynucleotide encoding SEQ ID NO: 45, and wherein expression and/or function of CDC42 in the modified T cell has been enhanced.

2. The modified T cell of claim 1, wherein the modified T cell has an increased level of cytokine release as compared to a corresponding T cell that does not have enhanced expression and/or function of CDC42.

3. The modified T cell of claim 2, wherein the cytokine comprises IFNγ.

4. The modified T cell of claim 3, wherein the comprises Granzyme B (GRAM B).

5. The modified T cell of claim 1, wherein the modified T cell has an increased level of protease release as compared to a corresponding T cell that does not have enhanced expression and/or function of CDC42.

6. The modified T cell of claim 1, wherein the modified cell has an enhanced migration capability as compared to a corresponding T cell that does not have enhanced expression and/or function of CDC42.

7. The modified T cell of claim 6, wherein the modified cell has enhanced migration in response to a chemokine.

8. The modified T cell of claim 7, wherein the chemokine is CCL5.

9. The modified T cell of claim 1, wherein the polynucleotide comprises SEQ ID NO:43 42.

10. The modified T cell of claim 1, wherein the polynucleotide is present in the modified cell in a recombinant DNA construct, in an mRNA, or in a viral vector.

11. The modified T cell of claim 10, wherein the polynucleotide is regulated by a promoter comprising a binding site for a transcription modulator that modulates the expression of the CDC42 in the modified T cell.

12. The modified T cell of claim 11, wherein the transcription modulator comprises Hif1a, NFAT, FOXP3, and/or NFkB.

13. A pharmaceutical composition comprising a population of the modified T cells of claim 1.

14. A method of causing or eliciting T cell response in a subject in need thereof, the method comprising administering an effective amount of the pharmaceutical composition of claim 13 to the subject.

15. An isolated nucleic acid comprising a polynucleotide encoding SEQ ID NO: 45.

* * * * *